(12) United States Patent
Kato

(10) Patent No.: US 11,517,207 B2
(45) Date of Patent: Dec. 6, 2022

(54) BAROREFLEX VASCULAR SYMPATHETIC NERVOUS ACTIVITY DETECTION DEVICE, BAROREFLEX VASCULAR SYMPATHETIC NERVOUS ACTIVITY DETECTION PROGRAM, AND BAROREFLEX VASCULAR SYMPATHETIC NERVOUS ACTIVITY DETECTION METHOD

(71) Applicant: SAPPORO MEDICAL UNIVERSITY, Sapporo (JP)

(72) Inventor: Yuichi Kato, Sapporo (JP)

(73) Assignee: SAPPORO MEDICAL UNIVERSITY, Sapporo (JP)

( * ) Notice: Subject to any disclaimer, the term of this patent is extended or adjusted under 35 U.S.C. 154(b) by 438 days.

(21) Appl. No.: 16/498,839

(22) PCT Filed: Mar. 30, 2018

(86) PCT No.: PCT/JP2018/013525
§ 371 (c)(1),
(2) Date: Sep. 27, 2019

(87) PCT Pub. No.: WO2018/181851
PCT Pub. Date: Oct. 4, 2018

(65) Prior Publication Data
US 2020/0113455 A1   Apr. 16, 2020

(30) Foreign Application Priority Data
Mar. 30, 2017   (JP) .............................. JP2017-067476

(51) Int. Cl.
*A61B 5/021*   (2006.01)
*A61B 5/0295*   (2006.01)
*A61B 5/00*   (2006.01)

(52) U.S. Cl.
CPC ........ *A61B 5/02108* (2013.01); *A61B 5/0295* (2013.01); *A61B 5/4035* (2013.01)

(58) Field of Classification Search
CPC combination set(s) only.
See application file for complete search history.

(56) References Cited

U.S. PATENT DOCUMENTS 9,826,909 B2    11/2017  Kato
2016/0029909 A1*  2/2016  Kato ................. A61B 5/02125
                                                          600/480

FOREIGN PATENT DOCUMENTS

JP    2008086568 A  *  4/2008
WO   2014/157605 A1   10/2014

OTHER PUBLICATIONS

Y. Sawada, et al. "Normalized pulse volume (NPV) derived photo-plethysmographically as a more valid measure of the finger vascular tone, International Journal of Psychophysiology, 2001, vol. 41", p. 1-10, Elsevier B.V.

(Continued)

*Primary Examiner* — Yi-Shan Yang
(74) *Attorney, Agent, or Firm* — Muncy, Geissler, Olds & Lowe, P.C.

(57) ABSTRACT

A vascular baroreflex-related sympathetic activity (VBRSA) detection device, a VBRSA detection program, and a VBRSA detection method capable of detecting in a simple and non-invasive manner VBRSA, which is sympathetic nervous activity of a blood vessel involved in a baroreflex function, are provided. The VBRSA detection device detects the VBRSA based on pulse wave data on a biological artery and a beat interval corresponding to the pulse wave data. The VBRSA detection device includes a VBRSA-series detecting unit that detects, as a VBRSA series indicative of VBRSA, a series where, from among the series in which the beat interval increases or decreases by n (n is a natural (Continued)

number 3 or more) beats consecutively, a correlation coefficient for the beat interval and pulse wave data is greater than any positive threshold up to the (n-1)-th beat and the correlation coefficient at the n-th beat falls to or below the threshold.

15 Claims, 22 Drawing Sheets

(56) References Cited

OTHER PUBLICATIONS

G. Sundlof, et al., "Human muscle nerve sympathetic activity at rest. Relationship to blood pressure and age, The Journal of Physiology, 1978, vol. 274," p. 621-637, The Physiological Society.

\* cited by examiner

[Fig.1]
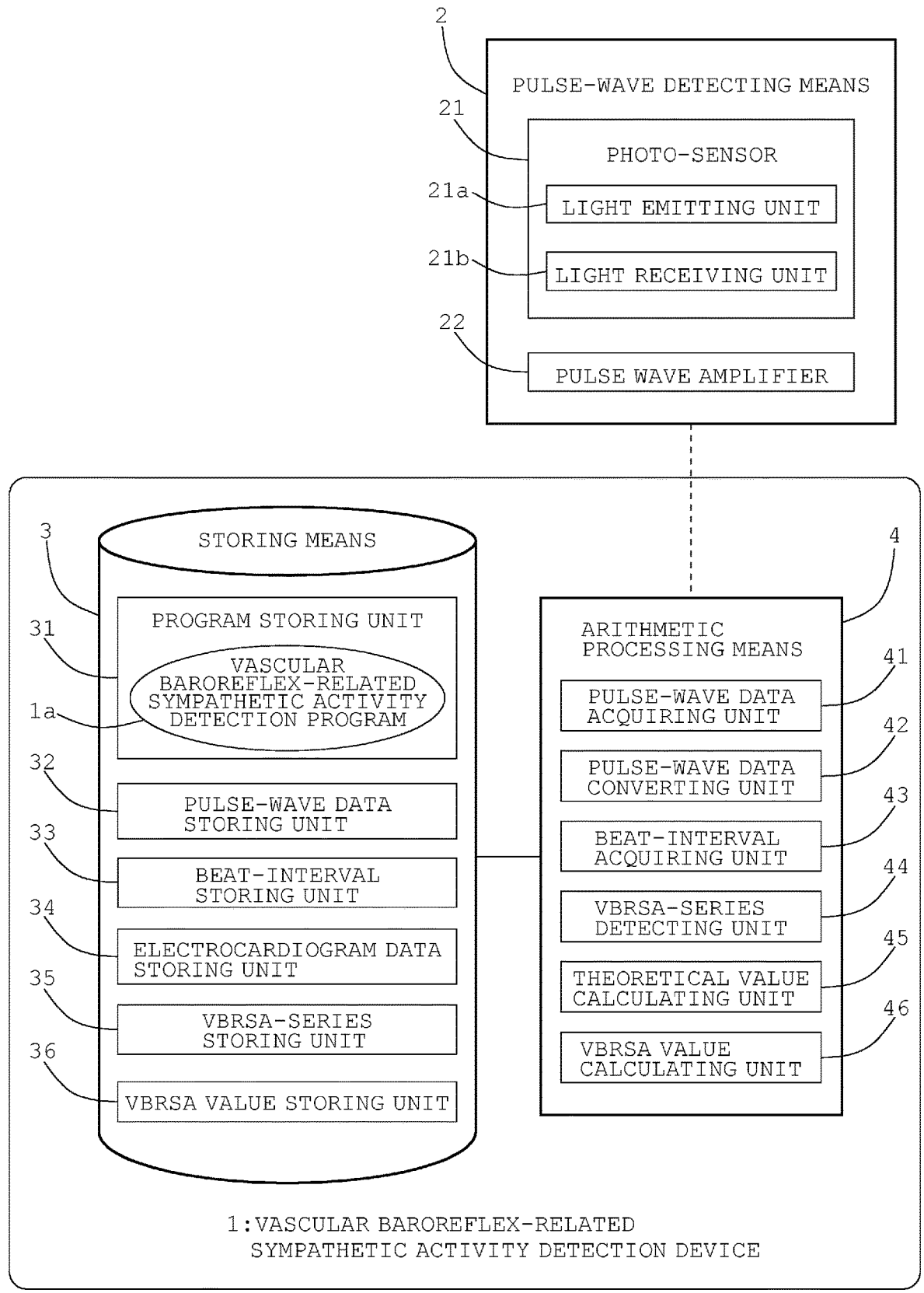

[Fig.2A]
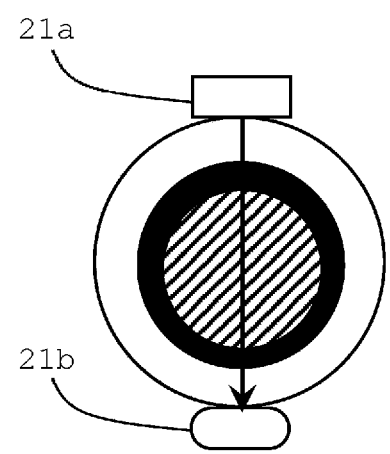

[Fig.2B]
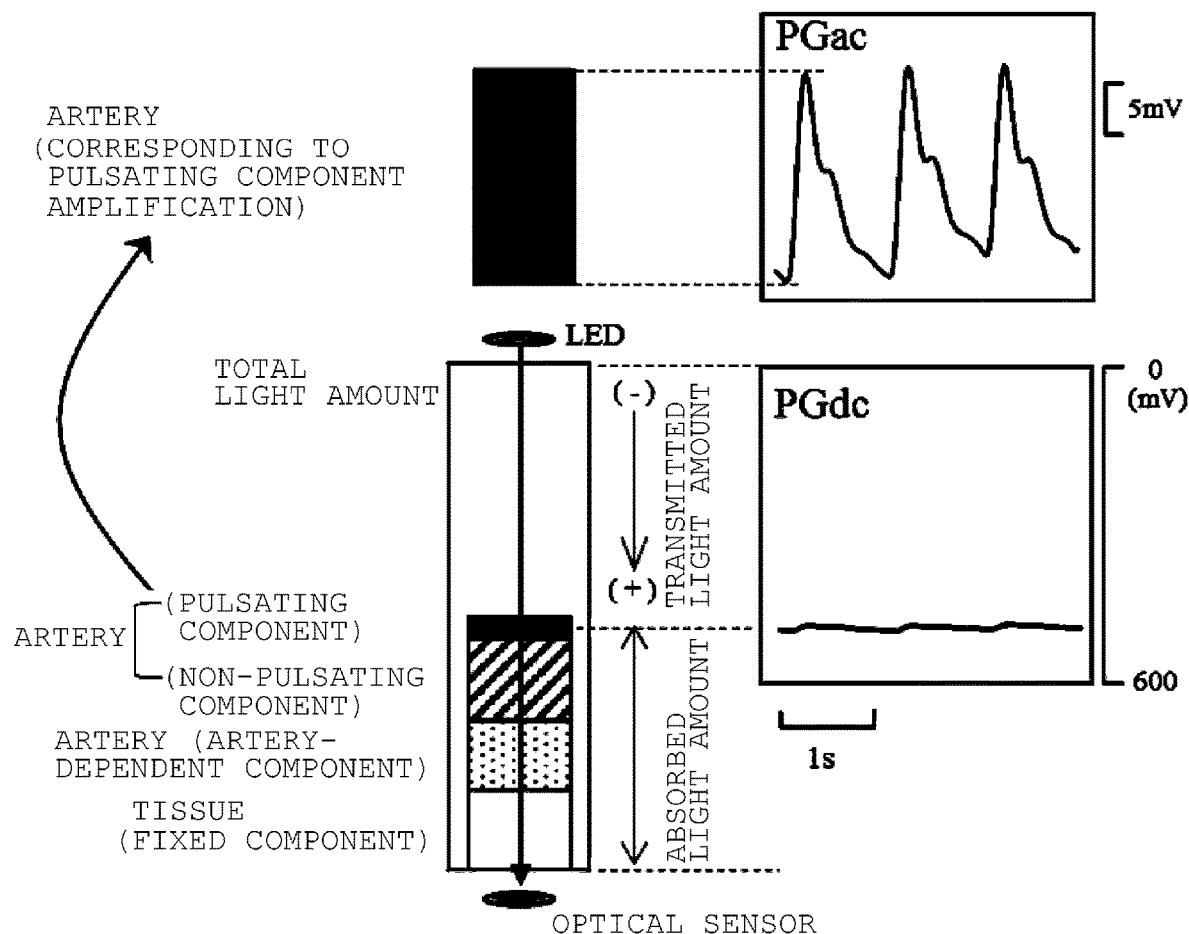

[Fig.3]
ELECTROCARDIOGRAM
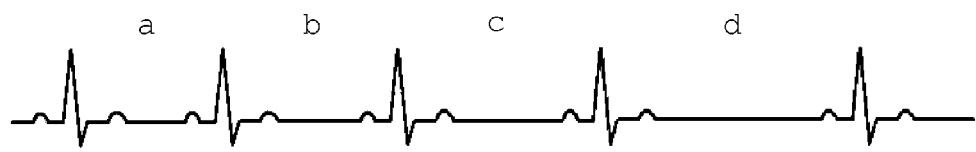
PULSE-WAVE
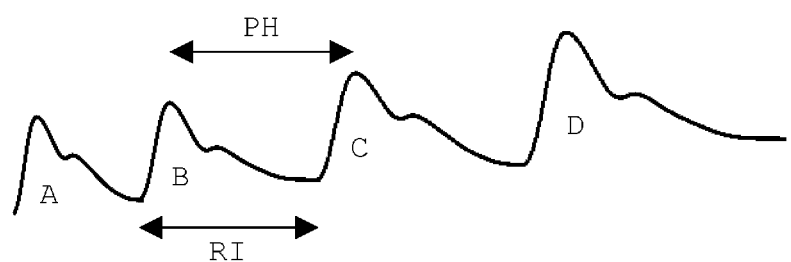

[Fig.4A]
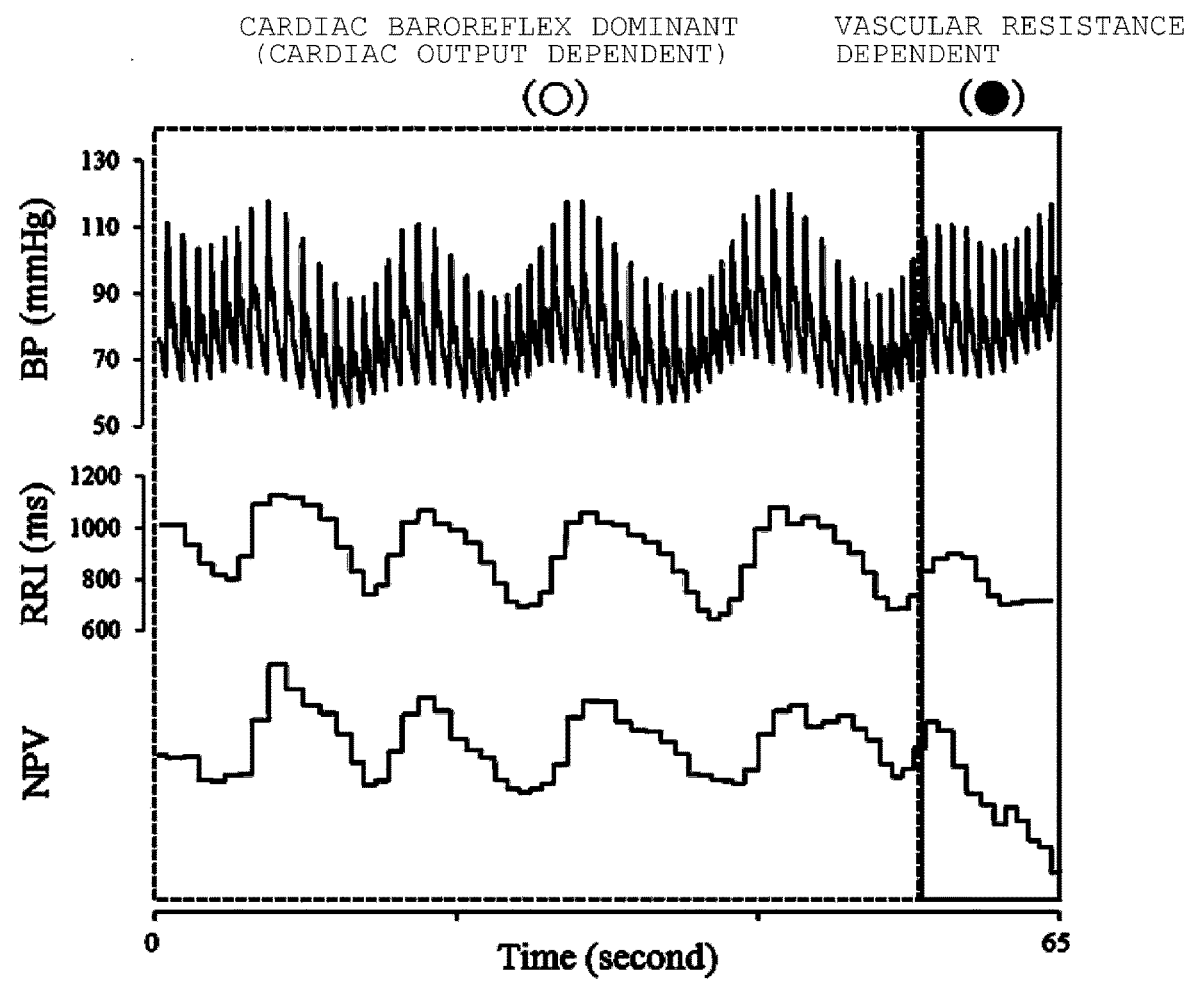

[Fig.4B]
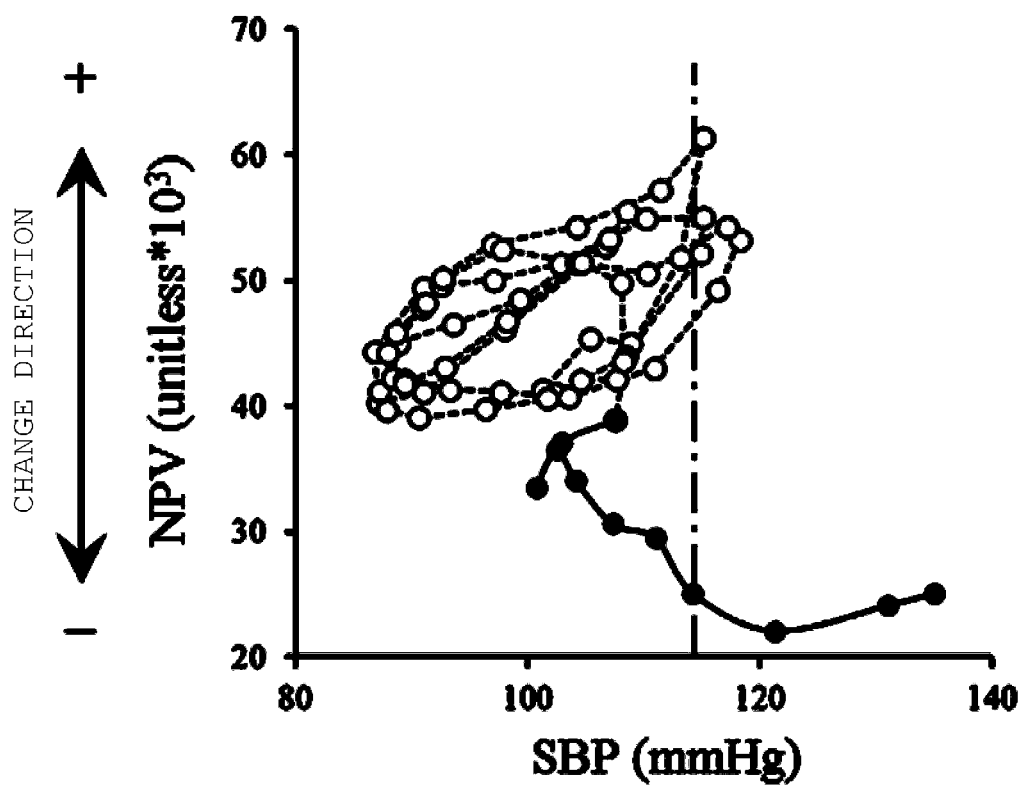

[Fig.5A]
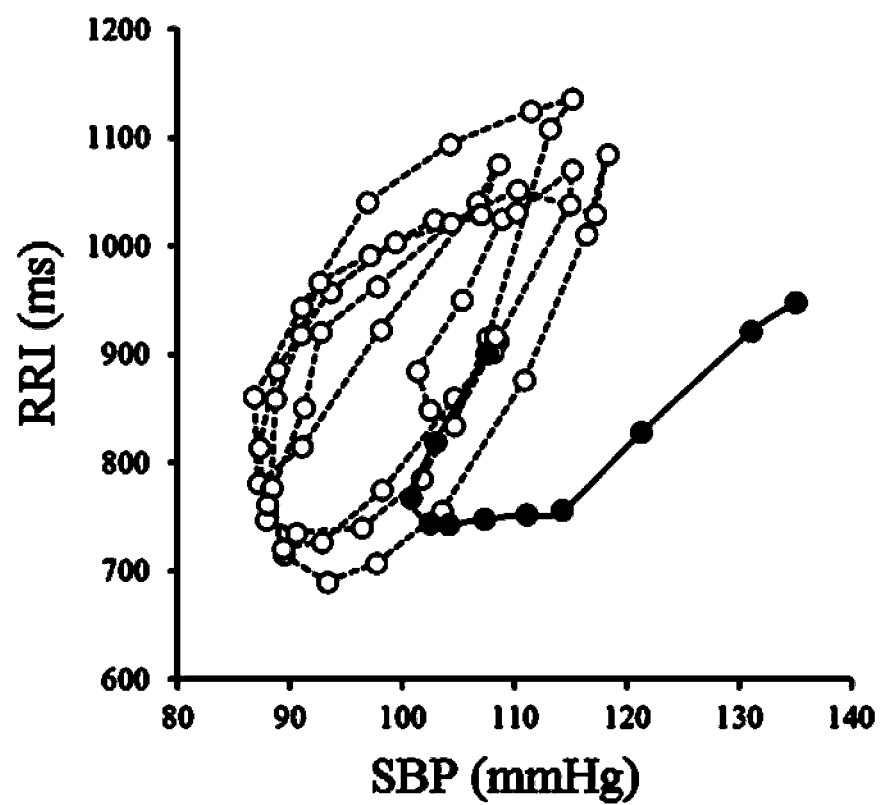

[Fig.5B]
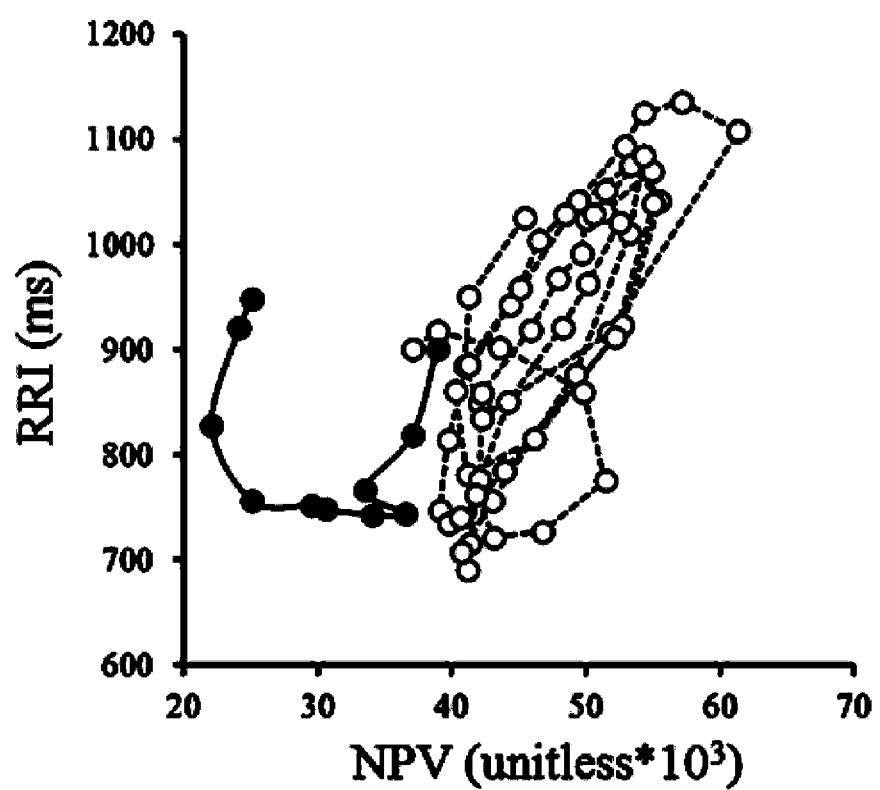

[Fig.6]
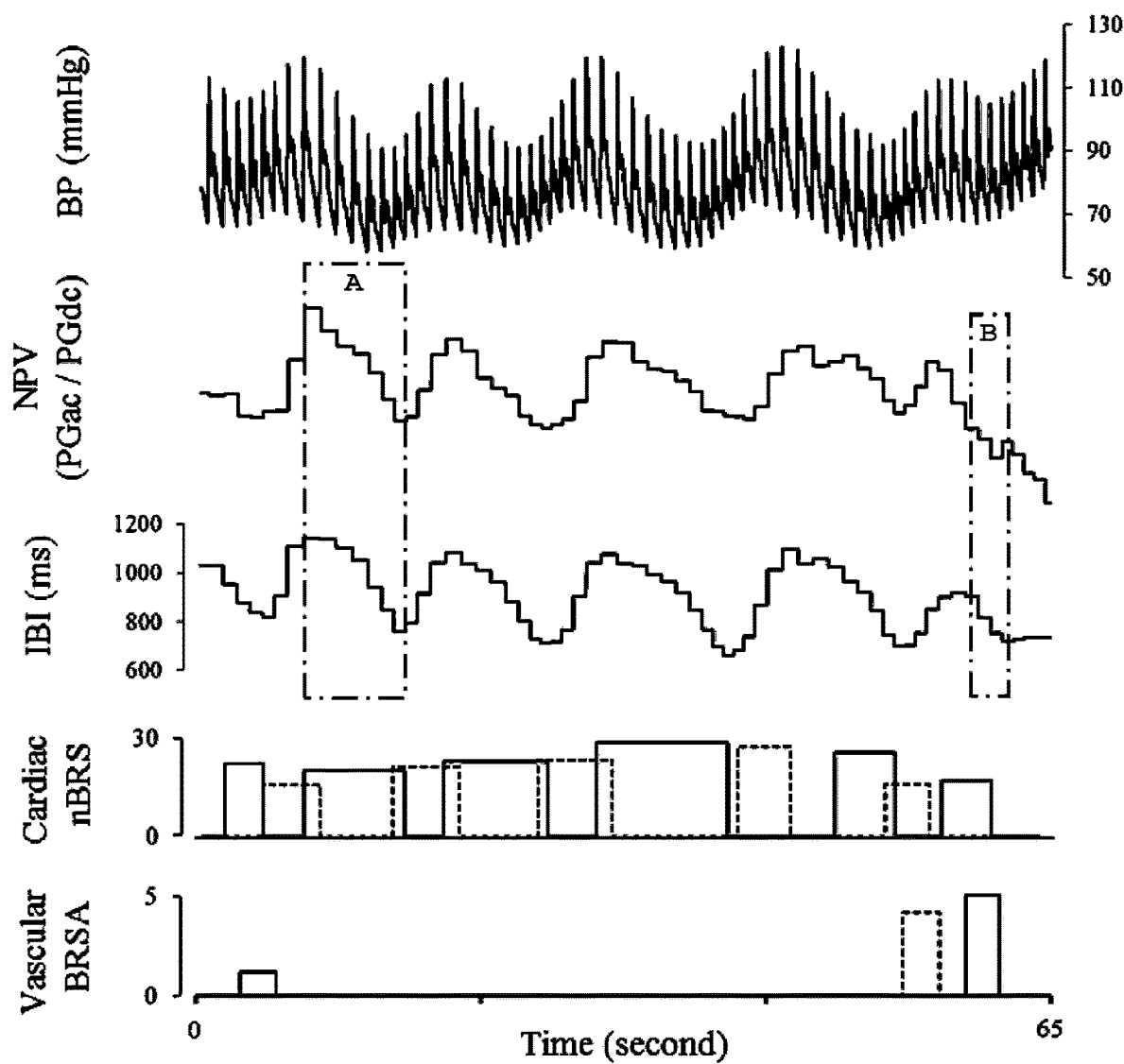

[Fig.7A]
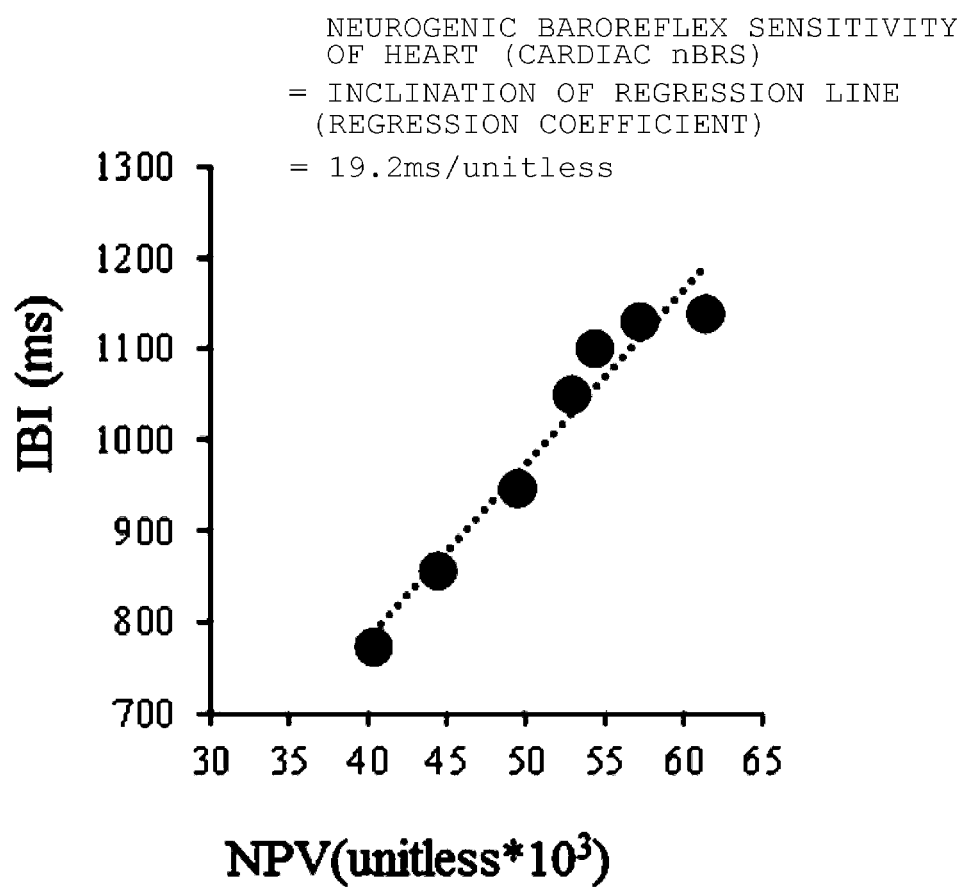

[Fig.7B]
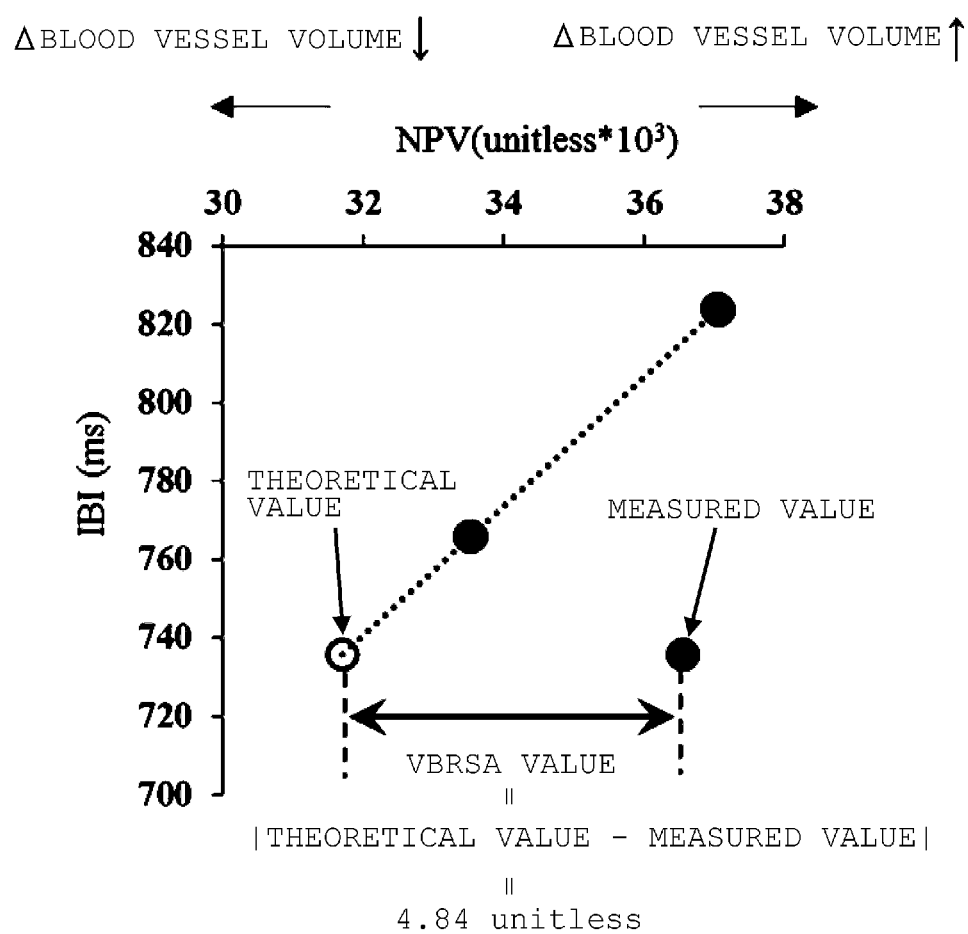

[Fig.8]
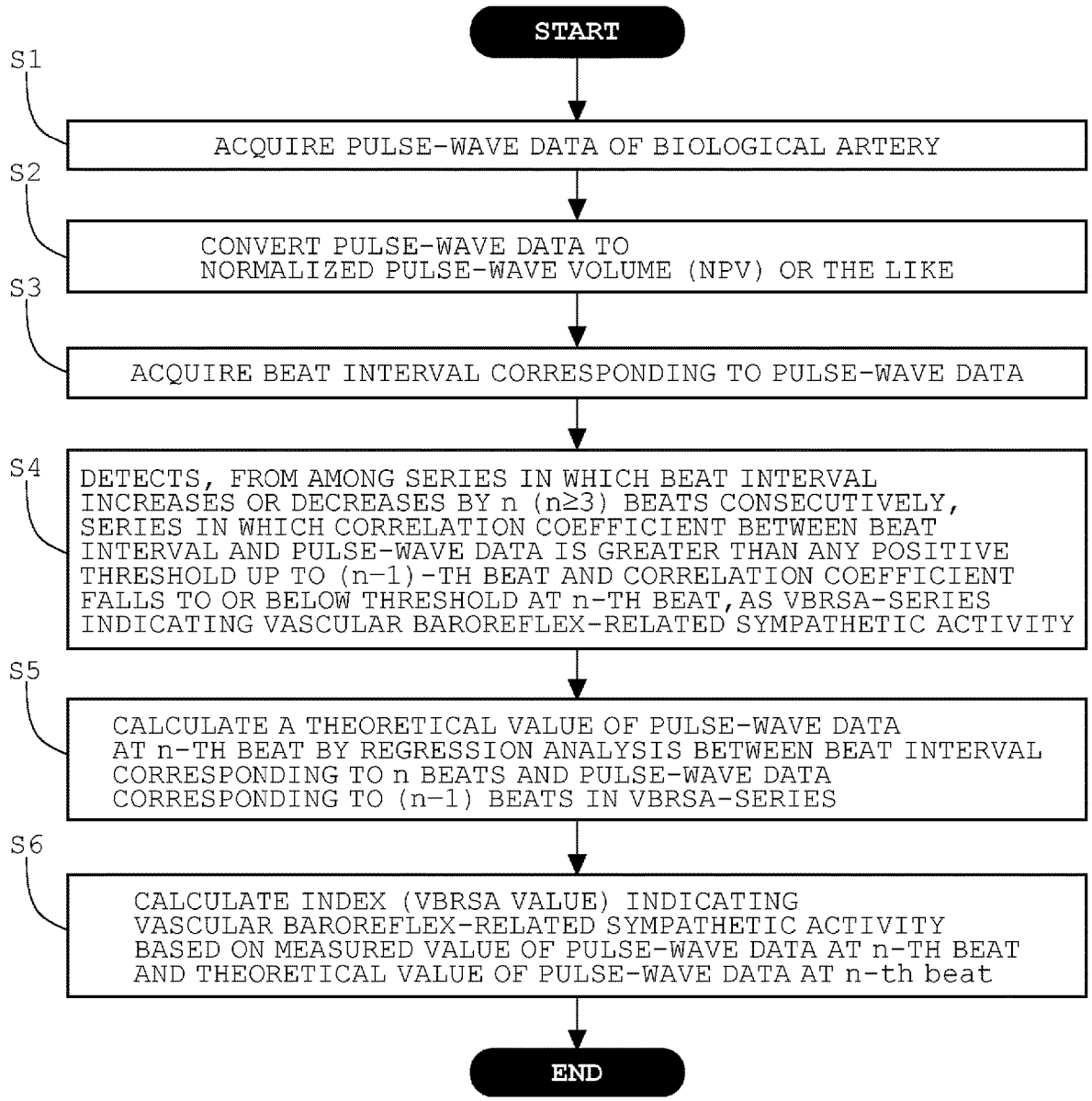

[Fig.9]
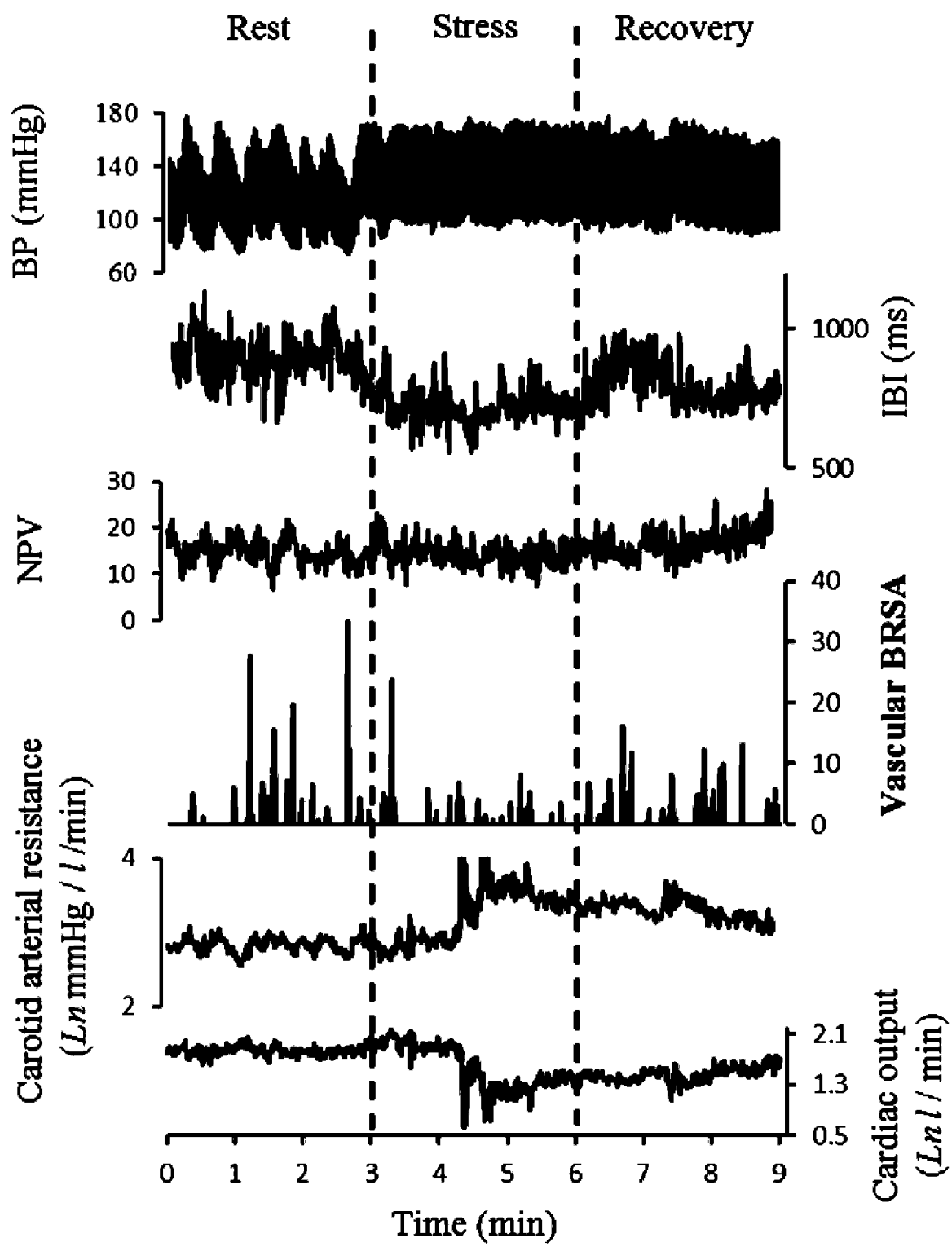

[Fig.10]
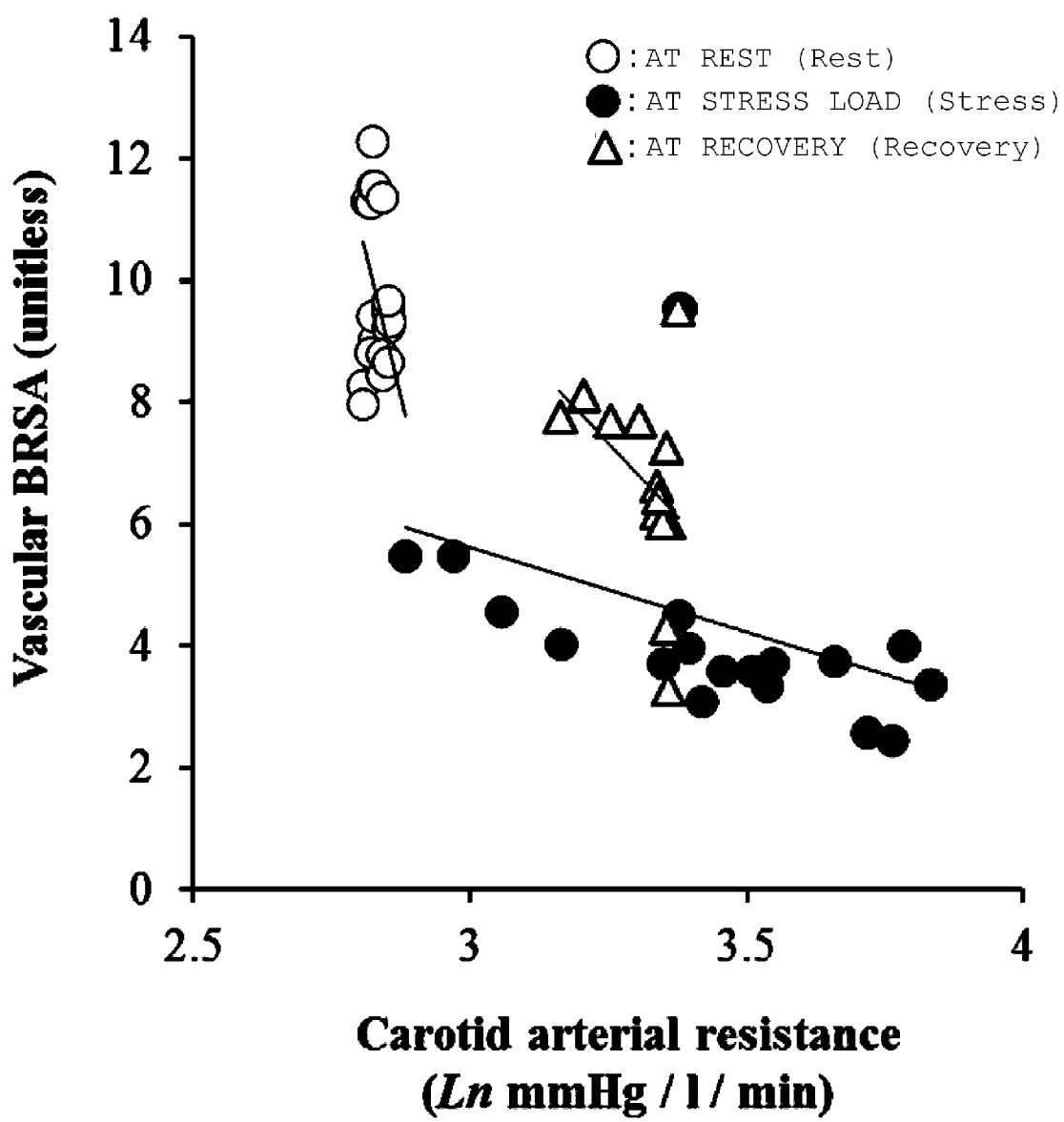

[Fig.11A]
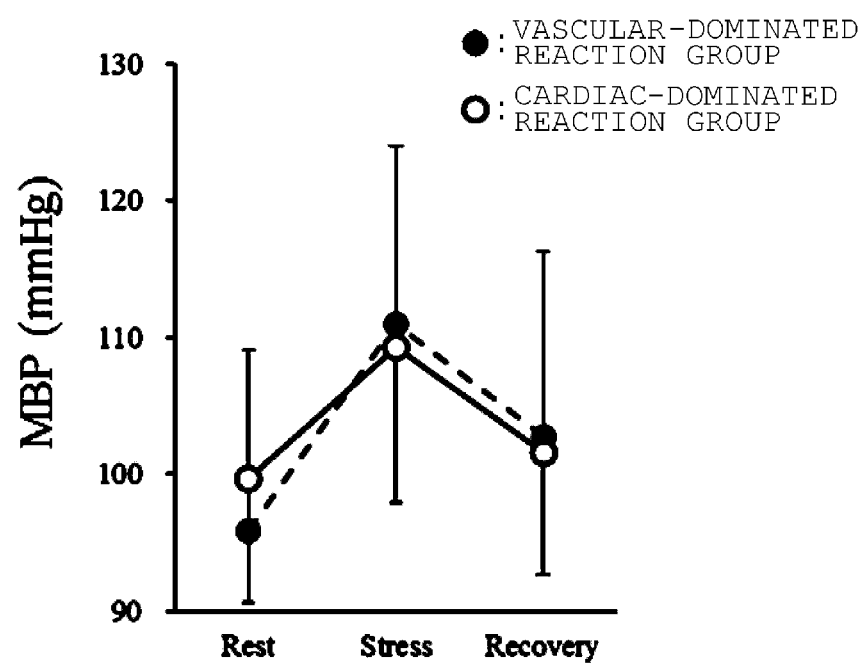

[Fig.11B]
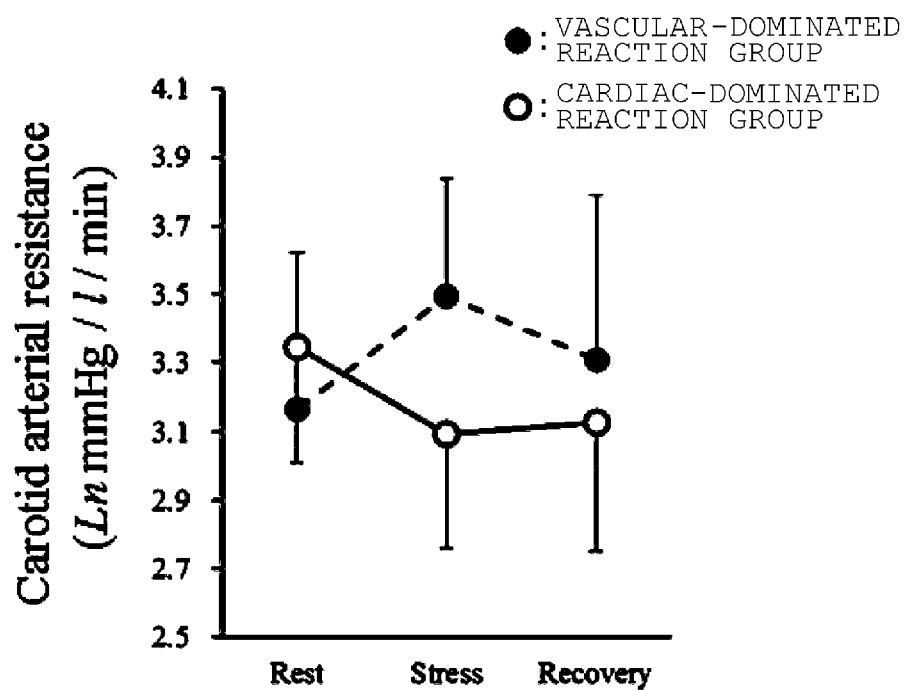

[Fig.11C]
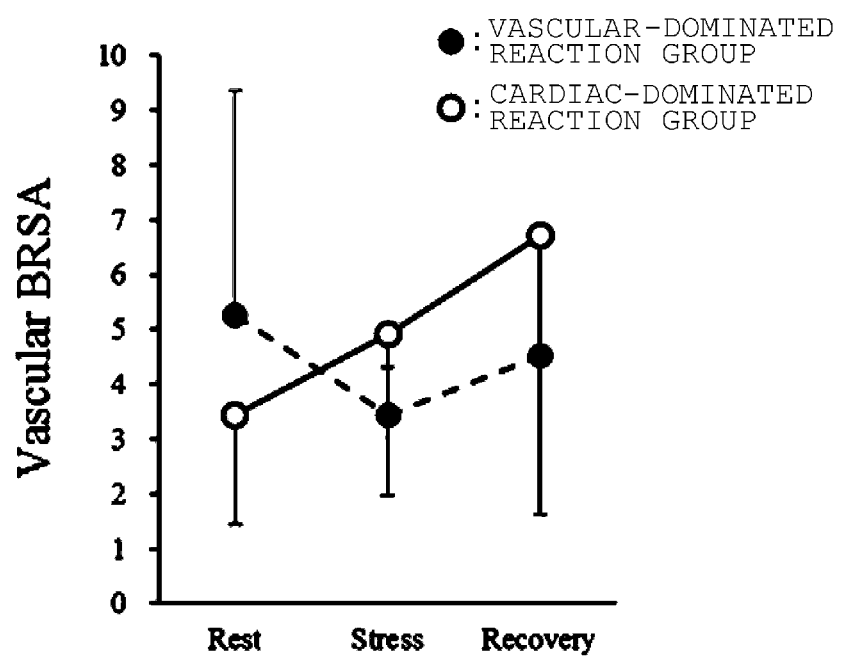

[Fig.12]
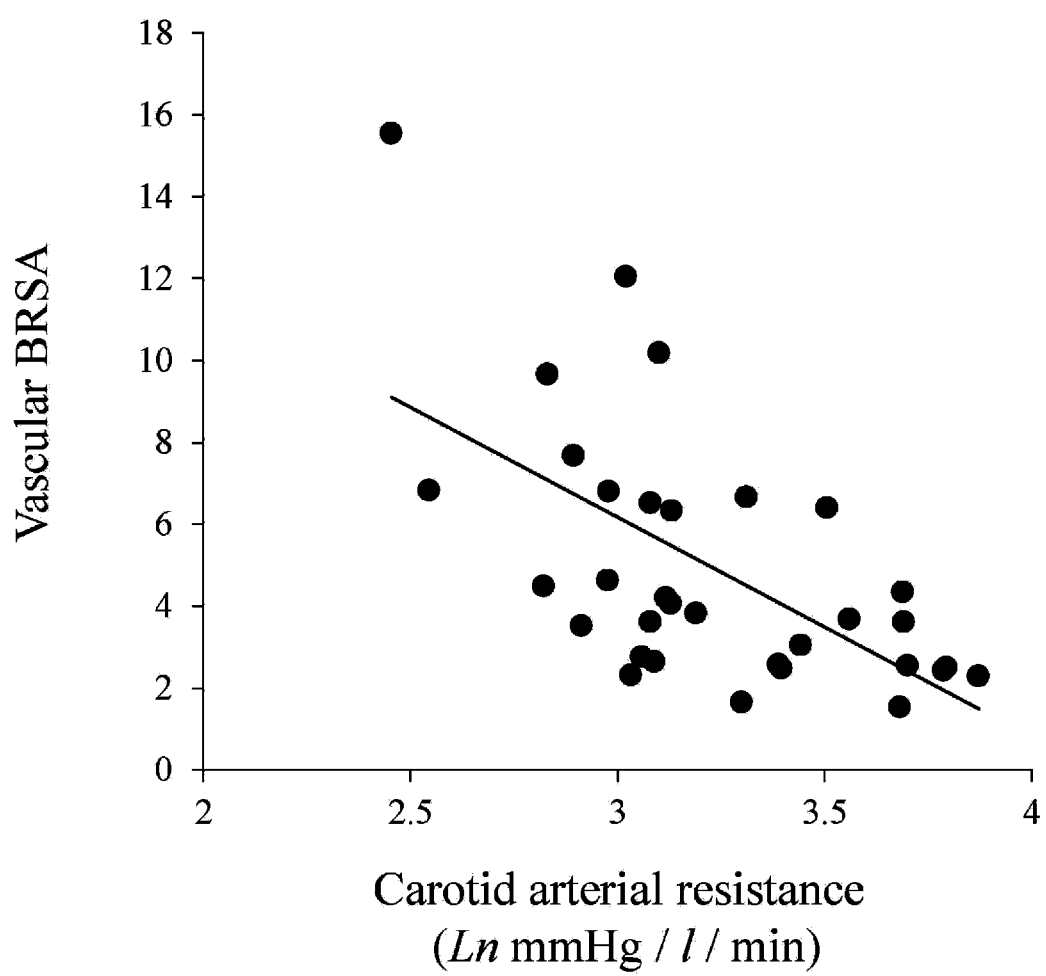

[Fig.13]
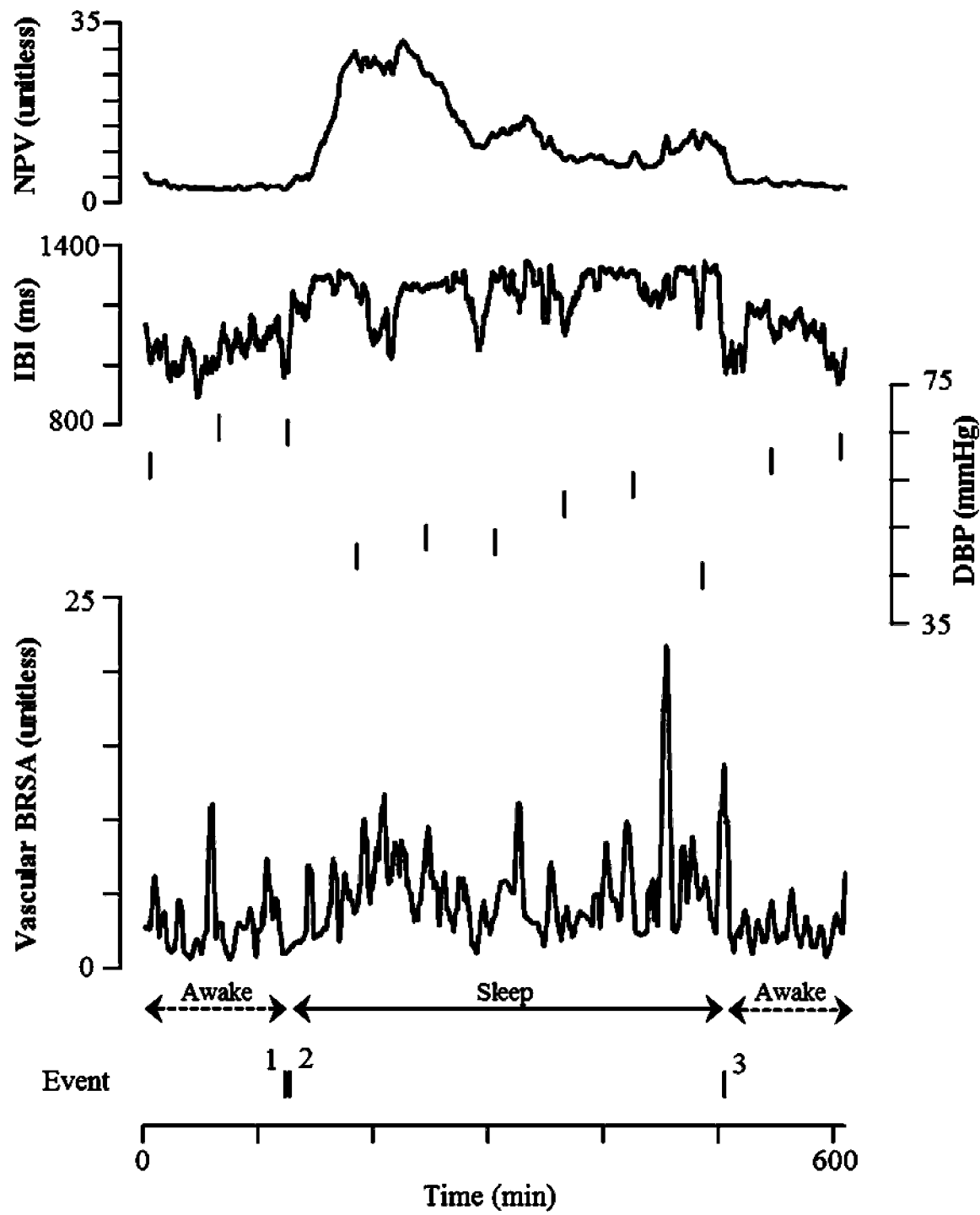

[Fig.14]
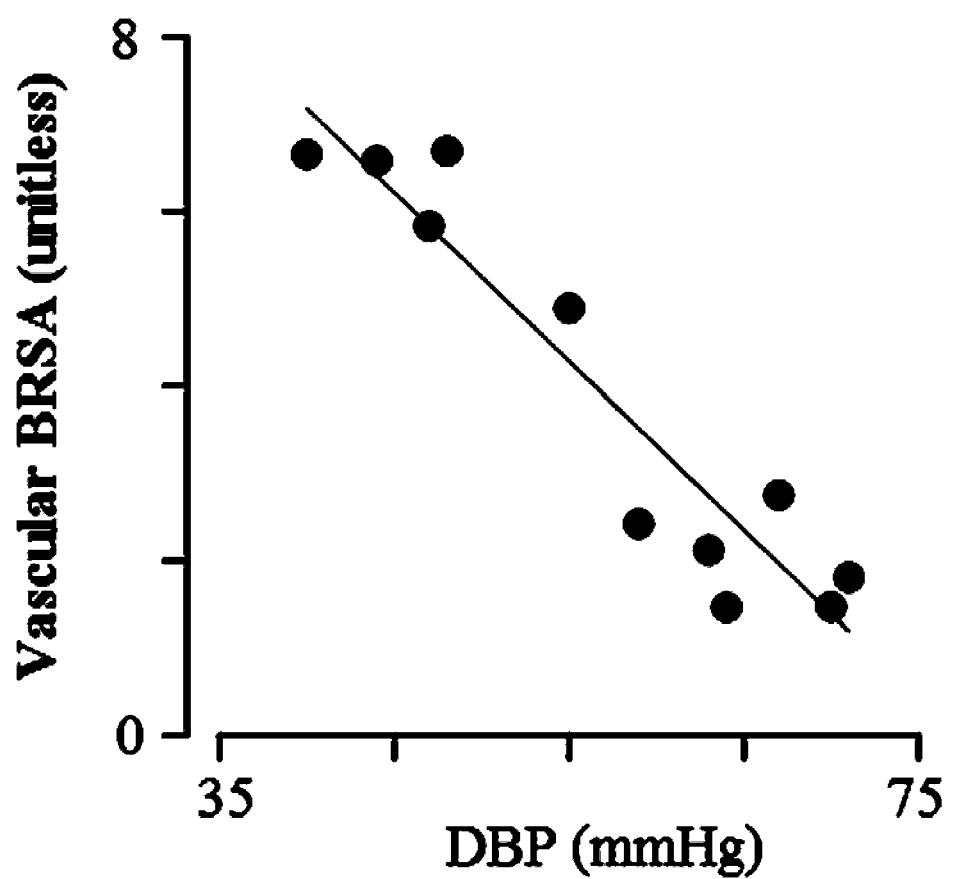

[Fig.15]
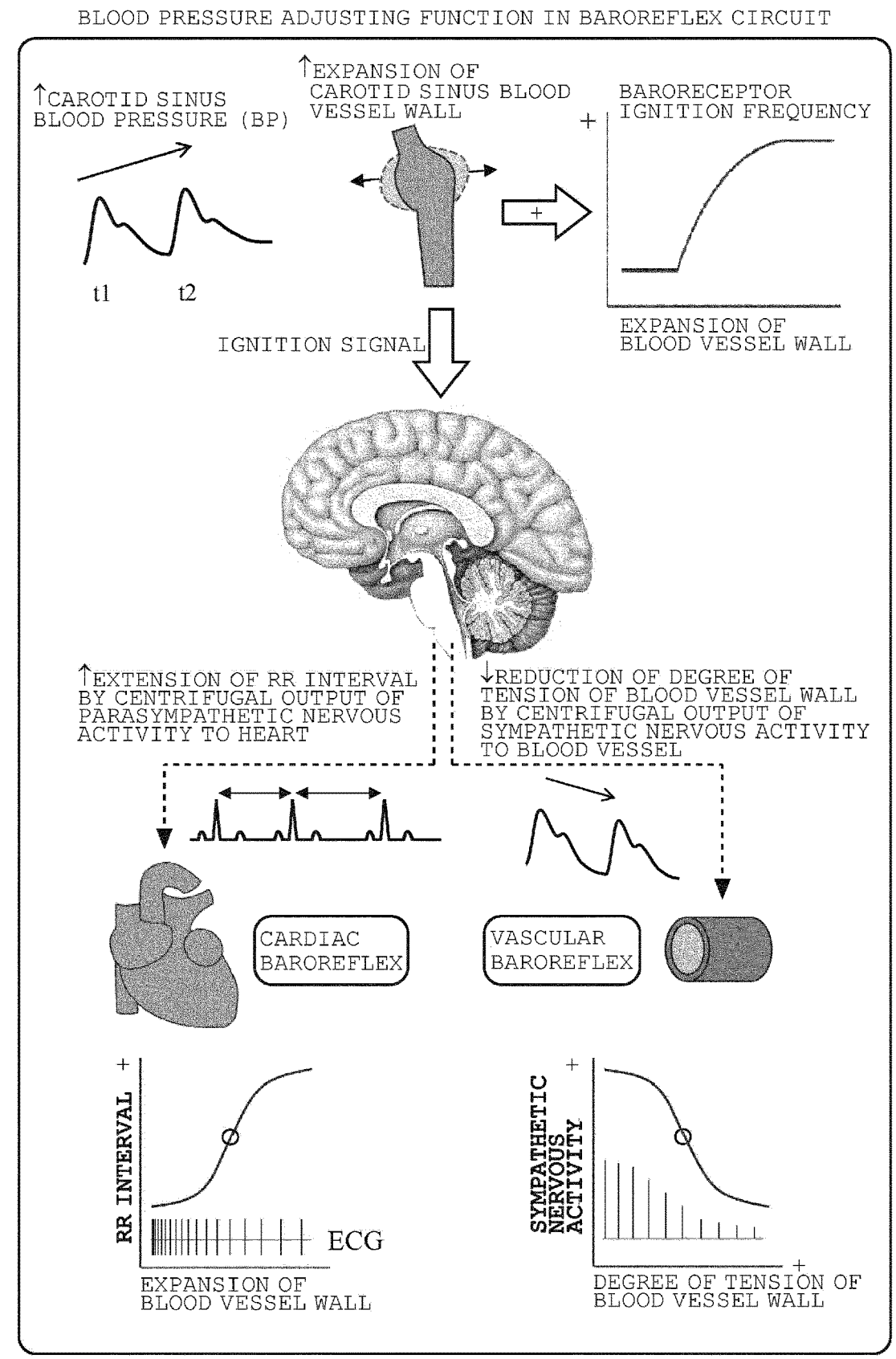

[Fig.16]
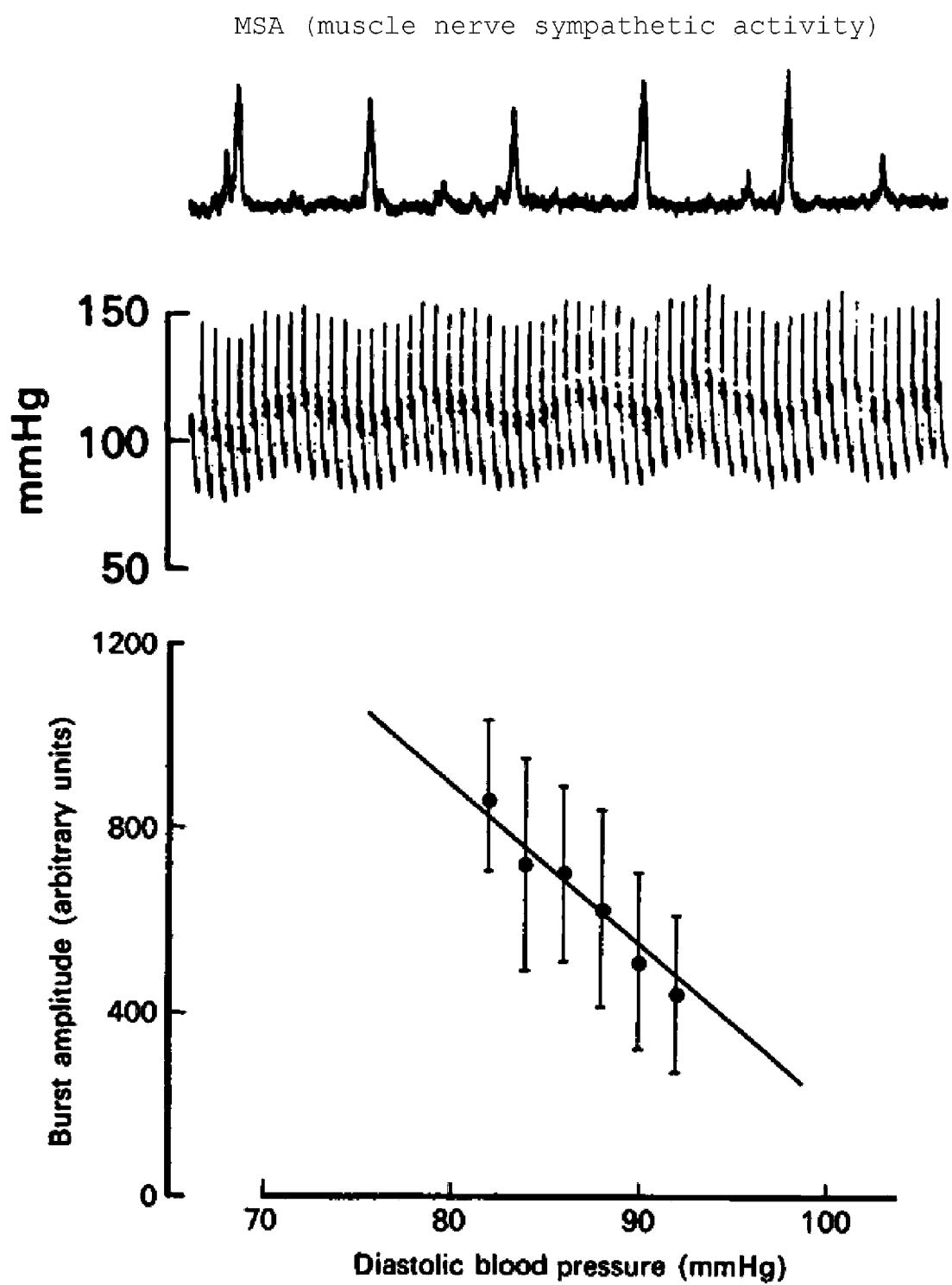

BAROREFLEX VASCULAR SYMPATHETIC NERVOUS ACTIVITY DETECTION DEVICE, BAROREFLEX VASCULAR SYMPATHETIC NERVOUS ACTIVITY DETECTION PROGRAM, AND BAROREFLEX VASCULAR SYMPATHETIC NERVOUS ACTIVITY DETECTION METHOD

TECHNICAL FIELD

The present invention relates to a vascular baroreflex-related sympathetic activity detection device, a vascular baroreflex-related sympathetic activity detection program, and a vascular baroreflex-related sympathetic activity detection method that non-invasively detect vascular sympathetic nervous activity associated with a baroreflex function that plays a role of keeping blood pressure constant.

BACKGROUND ART

It is conventionally known that blood pressure is an important risk factor for cardiovascular disease, cerebral infarction or the like. Therefore, by daily monitoring the status of blood pressure, it is possible to use the status of blood pressure as a guideline for preventing the aforementioned cardiovascular disease, cerebral infarction or the like, or as a diagnostic material in a pre-clinical stage. However, the act of measuring a blood pressure becomes a burden on the body and is a troublesome work, and so it is practically difficult to monitor the blood pressure daily or continuously.

Therefore, in recent years, a study of evaluating the baroreflex function of the autonomic nervous system trying to keep the blood pressure within a certain range is underway. This is because a reduction of the baroreflex function is considered as a risk factor for cerebral apoplexy, hypertension, faint, or the like. However, the blood pressure is hemodynamically defined as the product of cardiac output (single cardiac output×heart rate) and vascular resistance, whereas in baroreflex, the contribution of sympathetic nervous activity of the heart to the heart rate is not seen, and so the heart rate is controlled by parasympathetic nervous activity of the heart and the vascular resistance is controlled by vascular sympathetic nervous activity. Therefore, both parasympathetic nervous activity of the heart (neurogenic baroreflex function of the heart) and vascular sympathetic nervous activity (vascular neurogenic baroreflex function) are associated with the baroreflex function.

More specifically, as shown in FIG. 15, in the neurogenic baroreflex function of the heart, when the blood vessel wall expands due to an increase in the blood pressure, baroreceptor cells existing in the carotid or the like ignite. The brain that has received the ignition signal reduces the cardiac output via parasympathetic nervous activity of the heart (that is, by increasing the heartbeat interval or beat interval), trying to lower cardiac output and lower the blood pressure. On the other hand, the neurogenic baroreflex function of the blood vessel tries to increase the blood pressure by activating vascular sympathetic nervous activity and increasing the blood pressure so that the blood pressure does not fall to or below a predetermined value when the blood pressure drops due to relaxation of the blood vessel.

However, there is an individual difference in the operating balance between the neurogenic baroreflex function of the heart and the neurogenic baroreflex function of the blood vessel, and there are people whose neurogenic baroreflex function of the heart works dominantly or there are people whose vascular neurogenic baroreflex function works dominantly. Even in the same individual, for example, the operating balance may change when the individual is at rest and after doing exercise. Therefore, in order to evaluate the baroreflex function comprehensively, it is necessary to measure the neurogenic baroreflex function of the heart and the neurogenic baroreflex function of the blood vessel separately.

An example of the technique for measuring the neurogenic baroreflex function of the heart is a method for non-invasively measuring the function as sensitivity. For example, a so-called sequence method is known in which an increase or decrease in the diameter of a blood vessel due to expansion of the blood vessel wall is measured for each beat using an ultrasonic echo and the neurogenic baroreflex function is detected based on a baroreflex-series of the heart appearing as an accompanying extension or contraction of heartbeat or beat interval. The present inventor proposes a method for measuring neurogenic baroreflex sensitivity of the heart using a blood volume based on a normalized pulse-wave volume (Non-Patent Literature 1) instead of the blood vessel diameter (Patent Literature 1).

On the other hand, as a technique for measuring the neurogenic baroreflex function of the blood vessel, there is conventionally only a method for deriving it from a function of a diastolic blood pressure or vascular resistance as shown in FIG. 16, and vascular sympathetic nervous activity (MSA: muscle nerve sympathetic activity) of the blood vessel invasively measured by so-called microneurography (Non-Patent Literature 2).

CITATION LIST

Patent Literature

Patent Literature 1: WO2014/157605

Non Patent Literature

Non Patent Literature 1: Y. Sawada, et al. "Normalized pulse volume (NPV) derived photo-plethysmographically as a more valid measure of the finger vascular tone, International Journal of Psychophysiology, 2001, Vol. 41", p 1-10, Elsevier B.V.

Non-Patent Literature 2: G. Sundlof, et al., "Human muscle nerve sympathetic activity at rest. Relationship to blood pressure and age, The Journal of Physiology, 1978, Vol. 274," p 621-637, The Physiological Society.

SUMMARY OF INVENTION

Technical Problem

Although the aforementioned microneurography can directly measure vascular sympathetic nervous activity, it requires a minute metal electrode such as a needle to be inserted into the peripheral nerve bundle, resulting in a problem that microneurography is invasive. Conducting microneurography involves restrictions on the action such as having to go to a hospital to get an exam (staying quiet and rest), requiring well-prepared facilities (laboratory, examination room or the like) and skilled measurers, and also involves a problem that measurable time, place, situation or the like are extremely limited.

The present invention has been devised to solve such problems and it is an object of the present invention to provide a vascular baroreflex-related sympathetic activity detection device, a vascular baroreflex-related sympathetic activity detection program and a vascular baroreflex-related sympathetic activity detection method capable of simply and non-invasively detecting vascular baroreflex-related sympathetic activity which is vascular sympathetic nervous activity involved in a baroreflex function.

Solution to Problem

In order to solve a problem of simply and non-invasively detecting vascular baroreflex-related sympathetic activity which is vascular sympathetic nervous activity involved in a baroreflex function, a vascular baroreflex-related sympathetic activity detection device according to the present invention detects vascular baroreflex-related sympathetic activity which is vascular sympathetic nervous activity involved in a baroreflex function based on pulse-wave data of the biological artery and a beat interval corresponding to the pulse-wave data, the device including a VBRSA-series detecting unit that detects a series in which a correlation coefficient between the beat interval and the pulse-wave data is greater than any positive threshold up to an (n−1)-th beat and the correlation coefficient falls to or below the threshold at an n-th beat among the series, the beat interval of which increases or decreases by n (n is a natural number of 3 or more) beats consecutively as a vascular baroreflex-related sympathetic activity series (VBRSA-series) indicating the vascular baroreflex-related sympathetic activity. A vascular baroreflex-related sympathetic activity detection program according to the present invention causes a computer to function as the VBRSA-series detecting unit.

As an aspect of the vascular baroreflex-related sympathetic activity detection device according to the present invention, in order to solve the problem of indexing the vascular baroreflex-related sympathetic activity as a VBRSA value and simply and objectively evaluating the vascular baroreflex-related sympathetic activity, the vascular baroreflex-related sympathetic activity detection device may include a theoretical value calculating unit that calculates a theoretical value of the pulse-wave data at the n-th beat through a regression analysis between the beat interval corresponding to n beats and the pulse-wave data corresponding to (n−1) beats in the vascular baroreflex-related sympathetic activity series and a VBRSA value calculating unit that calculates a VBRSA value which is an index indicating the vascular baroreflex-related sympathetic activity based on a measured value of the pulse-wave data at the n-th beat and the theoretical value. Furthermore, as an aspect of the vascular baroreflex-related sympathetic activity detection program according to the present invention, the program may cause a computer to function as the theoretical value calculating unit and the VBRSA value calculating unit.

Furthermore, as an aspect of the present invention, in order to solve the problem of calculating a VBRSA value suitable for evaluating vascular baroreflex-related sympathetic activity, the VBRSA value calculating unit may calculate the VBRSA value using any one of equations (1) to (3) below:

$$\text{VBRSA value} = |PVt - PVm| \qquad \text{equation (1)}$$

$$\text{VBRSA value} = |\ln(PVt) - \ln(PVm)| \qquad \text{equation (2)}$$

$$\text{VBRSA value} = |PVt/PVm| \qquad \text{equation (3)}$$

where, the respective symbols represent the following:
PVt: theoretical value of pulse-wave data
PVm: measured value of pulse-wave data.

Furthermore, as an aspect of the present invention, in order to solve the problem of grasping a tendency that varies depending on diseases and improving evaluation accuracy by individually calculating VBRSA values for an ascending series and a descending series respectively, the VBRSA value calculating unit may individually calculate the VBRSA values for an ascending series in which the beat interval increases for n beats consecutively among the VBRSA-series and the VBRSA values for a descending series in which the beat interval decreases for n beats consecutively among the VBRSA-series.

Furthermore, as an aspect of the present invention, in order to solve the problem of expressing an index indicating vascular baroreflex-related sympathetic activity in an easily understandable manner by calculating a total value of the ascending series and the descending series as a VBRSA value even when the number of detected VBRSA-series is small, the VBRSA value calculating unit may calculate a value totaling or averaging average values of the VBRSA value calculated for the ascending series and average values of the VBRSA value calculated for the descending series as the VBRSA value.

Furthermore, as an aspect of the present invention, in order to solve the problem of widely and generally grasping the trend of vascular baroreflex-related sympathetic activity by excluding errors caused by living tissue components using a normalized pulse-wave volume (NPV) which is a non-dimensional absolute amount and a normalized pulse-wave volume converted to a logarithmic value (ln NPV) and making comparable not only measurement results of the same individual but also measurement results among different individuals, the pulse-wave data may be any one of a photoelectric volume pulse wave, a normalized pulse-wave volume which is the normalized photoelectric volume pulse wave or the normalized pulse-wave volume converted to a logarithmic value.

Furthermore, in order to solve the problem of simply and non-invasively detecting vascular baroreflex-related sympathetic activity which is vascular sympathetic nervous activity involved in a baroreflex function, a vascular baroreflex-related sympathetic activity detection method according to the present invention is a vascular baroreflex-related sympathetic activity detection method for detecting vascular baroreflex-related sympathetic activity which is vascular sympathetic nervous activity involved in a baroreflex function based on pulse-wave data of the biological artery and a beat interval corresponding to the pulse-wave data, the method including a VBRSA-series detection step of detecting a series in which a correlation coefficient between the beat interval and the pulse-wave data is greater than any positive threshold up to an (n−1)-th beat and the correlation coefficient falls to or below the threshold at an n-th beat among the series in which the beat interval increases or decreases by n (n is a natural number of 3 or more) beats consecutively as a vascular baroreflex-related sympathetic activity series (VBRSA-series) indicating the vascular baroreflex-related sympathetic activity.

Furthermore, as an aspect of the vascular baroreflex-related sympathetic activity detection method according to the present invention, in order to solve the problem of indexing the vascular baroreflex-related sympathetic activity as a VBRSA value and simply and objectively evaluating the vascular baroreflex-related sympathetic activity, the vascular baroreflex-related sympathetic activity detection method may include a theoretical value calculation step of calculating a theoretical value of the pulse-wave data at the n-th beat through a regression analysis between the beat interval corresponding to n beats and the pulse-wave data corresponding to (n−1) beats in the vascular baroreflex-related sympathetic activity series and a VBRSA value calculation step of calculating a VBRSA value which is an index indicating the vascular baroreflex-related sympathetic activity based on the measured value of the pulse-wave data at the n-th beat and the theoretical value.

Furthermore, as an aspect of the present invention, in order to solve the problem of calculating a VBRSA value suitable for evaluating vascular baroreflex-related sympathetic activity, in the VBRSA value calculation step, the VBRSA value may be calculated using any one of equations (1) to (3) below:

$$\text{VBRSA value} = |PVt - PVm| \qquad \text{equation (1)}$$

$$\text{VBRSA value} = |\ln(PVt) - \ln(PVm)| \qquad \text{equation (2)}$$

$$\text{VBRSA value} = |PVt/PVm| \qquad \text{equation (3)}$$

where, the respective symbols represent the following:
PVt: theoretical value of pulse-wave data
PVm: measured value of pulse-wave data.

Furthermore, as an aspect of the present invention, in order to solve the problem of grasping a tendency that varies depending on diseases and improving evaluation accuracy by individually calculating VBRSA values for an ascending series and a descending series respectively, in the VBRSA value calculation step, the VBRSA values for the ascending series in which the beat interval increases for n beats consecutively among the VBRSA-series and the VBRSA values for the descending series in which the beat interval decreases for n beats consecutively among the VBRSA-series may be individually calculated.

Furthermore, as an aspect of the present invention, in order to solve the problem of expressing an index indicating vascular baroreflex-related sympathetic activity in an easily understandable manner by calculating a total value of the ascending series and the descending series as a VBRSA value even when the number of detected VBRSA-series is small, in the VBRSA value calculation step, a value totaling or averaging average values of the VBRSA value calculated for the ascending series and average values of the VBRSA value calculated for the descending series as the VBRSA value may be calculated.

Advantageous Effects of Invention

According to the present invention, it is possible to simply and non-invasively detect vascular baroreflex-related sympathetic activity which is vascular sympathetic nervous activity involved in a baroreflex function.

BRIEF DESCRIPTION OF DRAWINGS

FIG. 1 is a block diagram illustrating an embodiment of a vascular baroreflex-related sympathetic activity detection device and a vascular baroreflex-related sympathetic activity detection program according to the present invention.

FIG. 2A is a cross-sectional view illustrating a situation in which a photoelectric volume pulse wave of a biological tissue (vain part is omitted) is measured and FIG. 2B is a diagram describing an AC component (PGac) and a DC component (PGdc) of a photoelectric volume pulse wave.

FIG. 3 is a diagram describing a "beat interval" and a "beat interval corresponding to pulse-wave data" according to the present invention.

FIG. 4A illustrates measured data of a blood pressure (BP), a heartbeat interval (RRI) and a normalized pulse-wave volume (NPV) and FIG. 4B is a scattered graph of a systolic blood pressure (SBP) and a normalized pulse-wave volume (NPV) in the measured data.

FIG. 5A is a scattered graph of the systolic blood pressure (SBP) and the heartbeat interval (RRI) in the measured data in FIG. 4A and FIG. 5B is a scattered graph of the normalized pulse-wave volume (NPV) and the heartbeat interval (RRI).

FIG. 6 is a diagram illustrating a detection time and measurement result of neurogenic baroreflex sensitivity (cardiac nBRS) of the heart and vascular baroreflex-related sympathetic activity series (VBRSA-series) in the measured data.

FIG. 7A is a diagram illustrating a method for measuring neurogenic baroreflex sensitivity (cardiac nBRS) of the heart and FIG. 7B is a diagram illustrating a method for calculating vascular baroreflex-related sympathetic activity (vascular BRSA).

FIG. 8 is a flowchart illustrating an embodiment of a vascular baroreflex-related sympathetic activity detection method according to the present invention.

FIG. 9 is a graph illustrating measured data of an individual according to Example 1.

FIG. 10 is a scattered graph of a VBRSA value (vascular BRSA) and vascular resistance (carotid arterial resistance) of carotid in the measured data in FIG. 9.

FIG. 11A is a graph illustrating a mean blood pressure (MBP), FIG. 11B is a graph illustrating vascular resistance (carotid arterial resistance) of carotid and FIG. 11C is a graph illustrating a VBRSA value (vascular BRSA) measured for different groups with different reaction mechanisms corresponding to mental stress according to Example 2.

FIG. 12 is a correlation diagram between VBRSA value (vascular BRSA) and vascular resistance (carotid arterial resistance) of carotid about measured data of all examinees according to Example 2.

FIG. 13 is a graph illustrating measured data in daily life according to Example 3.

FIG. 14 is a correlation diagram between a VBRSA value and a diastolic blood pressure (DBP) during a blood pressure measurement period of the measured data in FIG. 13.

FIG. 15 is a diagram describing a mechanism associated with a baroreflex function.

FIG. 16 is a diagram illustrating a relationship between vascular sympathetic nervous activity (MSA) using conventional microneurography and a diastolic blood pressure.

DESCRIPTION OF EMBODIMENTS

A vascular baroreflex-related sympathetic activity detection device, a vascular baroreflex-related sympathetic activity detection program and a vascular baroreflex-related sympathetic activity detection method according to the present invention are suitable for detecting vascular baroreflex-related sympathetic activity (vascular BRSA) which is vascular sympathetic nervous activity associated with a baroreflex function and indexing and evaluating the vascular baroreflex-related sympathetic activity.

As a result of keen research in view of the aforementioned problems, the present inventor has discovered that it is possible to simply and non-invasively detect vascular baroreflex-related sympathetic activity with high reliability individually using only pulse-wave data non-invasively measured from a living body.

Hereinafter, an embodiment of the vascular baroreflex-related sympathetic activity detection device, the vascular baroreflex-related sympathetic activity detection program and the vascular baroreflex-related sympathetic activity detection method according to the present invention will be described using the accompanying drawings.

As shown in FIG. 1, pulse-wave detecting means 2 for detecting a pulse wave of the biological artery in an ear, finger or the like is connected to the vascular baroreflex-related sympathetic activity detection device 1 of the present embodiment. The vascular baroreflex-related sympathetic activity detection device 1 also includes storing means 3 for storing a vascular baroreflex-related sympathetic activity detection program 1a and various data of the present embodiment and arithmetic processing means 4 for controlling the storing means 3, acquiring the various data and executing calculation processing. Hereinafter, the respective means will be described in detail.

Note that the vascular baroreflex-related sympathetic activity detection device 1 in the present embodiment is constructed of a personal computer provided with the storing means 3 and the arithmetic processing means 4, and the pulse-wave detecting means 2 is separately connected thereto as a peripheral device. However, the device configuration is not limited to the above configuration. For example, the vascular baroreflex-related sympathetic activity detection program 1a of the present embodiment may be implemented as an application, installed in a smartphone or a tablet terminal, which may be caused to function as the vascular baroreflex-related sympathetic activity detection device 1 of the present embodiment.

The pulse-wave detecting means 2 non-invasively detects a volume pulse wave indicating a pulsation volume change in the artery using a photo-plethysmography (PPG) method. In the present embodiment, the pulse-wave detecting means 2 includes a photo-sensor 21 attached to a living body to detect light amount as shown in FIG. 1, and a pulse wave amplifier 22 that amplifies an output signal from the photo-sensor 21 and outputs the signal as pulse-wave data.

The photo-sensor 21 is provided with a light emitting unit 21a fixed to the living body such as an LED (light emitting diode) and a light receiving unit 21b such as a photodiode disposed at a position opposite to the light emitting unit 21a across the living body. The amount of transmitted light emitted from the light emitting unit 21a and passed through the living body is detected by the light receiving unit 21b and outputted time-sequentially from the pulse wave amplifier 22 as pulse-wave data.

Note that the pulse wave amplifier 22 in the present embodiment outputs a photoelectric volume pulse wave as pulse-wave data. However, without being limited to this configuration, the pulse wave amplifier 22 may output the photoelectric volume pulse wave after converting it to a different value. More specifically, the pulse wave amplifier 22 may output normalized pulse-wave volume (normalized pulse volume: hereinafter referred to as "NPV") which is a normalized photoelectric volume pulse wave as pulse-wave data. Alternatively, the pulse wave amplifier 22 may output a normalized pulse-wave volume converted to a logarithmic value such as natural logarithm (ln NPV) of the normalized pulse-wave volume as pulse-wave data. Note that an example of a method for calculating a normalized pulse-wave volume (NPV) is a method whereby a photoelectric volume pulse wave is divided into a DC component and an AC component, and the amplitude of the AC component is divided by a mean value of the DC component at the same time. However, the present embodiment is not limited to the method, but any method may be adopted as long as the normalized pulse-wave volume (NPV) as the calculation result is the same.

In the present embodiment, the pulse-wave detecting means 2 acquires pulse-wave data of the biological artery from an ear, but the region to be detected is not limited to the ear. That is, any region can be used if a pulse wave of the biological artery can be detected by the pulse-wave detecting means 2, for example, finger, nose, palm, wrist, arm, and leg can be assumed as the region to be detected. Although a transmission type optical sensor such as a photodiode is used as the light receiving unit 21b in the present embodiment, a reflection type optical sensor such as a phototransistor may also be used.

Furthermore, the pulse-wave detecting means 2 is preferably configured to be wearable to enable monitoring of pulse wave simply and handily in daily life in a household environment or the like. Examples of such wearable pulse-wave detecting means 2 include earphone type or earring type that can be attached to the ear, bracelet type that can be attached to the wrist or upper arm, and ring type that can be attached to the finger. The pulse-wave detecting means 2 reduces burden when attached and allows the examinee to spend daily life without trouble even during monitoring.

The storing means 3 stores various data and functions as a working area when the arithmetic processing means 4 performs arithmetic processing. The storing means 3 in the present embodiment is constructed of a hard disk, a ROM (read only memory), a RAM (random access memory), a flash memory or the like and includes a program storing unit 31, a pulse-wave data storing unit 32, a beat-interval storing unit 33, an electrocardiogram data storing unit 34, a VBRSA-series storing unit 35 and a VBRSA value storing unit 36, as shown in FIG. 1.

A vascular baroreflex-related sympathetic activity detection program 1a of the present embodiment is installed in the program storing unit 31. When the arithmetic processing means 4 executes the vascular baroreflex-related sympathetic activity detection program 1a, a computer such as a personal computer, a smartphone or a tablet terminal is caused to function as each component which will be described later.

Note that a usage pattern of the vascular baroreflex-related sympathetic activity detection program 1a is not limited to the above configuration. The vascular baroreflex-related sympathetic activity detection program 1a may be stored in a non-transitory computer-readable recording medium such as a CD-ROM or a USB memory and may be directly read and executed from the recording medium. Furthermore, the vascular baroreflex-related sympathetic activity detection program 1a may be used from an external server or the like under a cloud computing scheme or ASP (application service provider) scheme.

The pulse-wave data storing unit 32 stores pulse-wave data acquired by a pulse-wave data acquiring unit 41 which will be described later or pulse-wave data converted by a pulse-wave data converting unit 42 which will be described later in time series. The beat-interval storing unit 33 stores beat intervals acquired by a beat-interval acquiring unit 43 which will be described later in time series. The electrocardiogram data storing unit 34 stores cardiogram data acquired by cardiogram acquiring means (not shown) such as an electrocardiograph in time series.

The VBRSA-series storing unit 35 stores a vascular baroreflex-related sympathetic activity series (VBRSA-series) detected by the VBRSA-series detecting unit 44 which will be described later. Furthermore, the VBRSA value storing unit 36 stores a VBRSA value which is an index indicating vascular baroreflex-related sympathetic activity calculated by a VBRSA value calculating unit 46 which will be described later.

The arithmetic processing means 4 is constructed of a CPU (central processing unit) or the like, and when the vascular baroreflex-related sympathetic activity detection program 1a is executed, the arithmetic processing means 4 functions as the pulse-wave data acquiring unit 41, the pulse-wave data converting unit 42, the beat-interval acquiring unit 43, the VBRSA-series detecting unit 44, the theoretical value calculating unit 45 and the VBRSA value calculating unit 46. Hereinafter, the respective components will be described more specifically.

The pulse-wave data acquiring unit 41 acquires pulse-wave data of the biological artery from the pulse-wave detecting means 2. The pulse-wave data acquiring unit 41 of the present embodiment acquires photoelectric volume pulse wave from the pulse-wave detecting means 2 as pulse-wave data. The pulse-wave data acquiring unit 41 provides the photoelectric volume pulse wave to the pulse-wave data converting unit 42 and causes the pulse-wave data converting unit 42 to convert the photoelectric volume pulse wave to a normalized pulse-wave volume (NPV).

Note that the pulse-wave data acquiring unit 41 is not limited to the above configuration, and when the pulse-wave detecting means 2 side converts a photoelectric volume pulse wave to a normalized pulse-wave volume (NPV) or a normalized pulse-wave volume converted to a logarithmic value (ln NPV) in advance, these volumes may be acquired as pulse-wave data. Furthermore, the photoelectric volume pulse wave may be used as pulse-wave data as is. In such a case, the pulse-wave data acquiring unit 41 directly stores the pulse-wave data acquired from the pulse-wave detecting means 2 in the pulse-wave data storing unit 32 in time series without providing the pulse-wave data to the pulse-wave data converting unit 42.

Furthermore, the pulse-wave data acquiring unit 41 of the present embodiment acquires pulse-wave data directly from the pulse-wave detecting means 2, but the present embodiment is not limited to this configuration. For example, pulse-wave data measured by other apparatuses may be collected from a recording medium such as a USB memory. Furthermore, the pulse-wave data saved in a data server or the like may be downloaded via the Internet or the like.

The pulse-wave data converting unit 42 converts the photoelectric volume pulse wave as pulse-wave data to a different value such as a normalized pulse-wave volume (NPV) or normalized pulse-wave volume converted to a logarithmic value (ln NPV). In the present invention, it is preferable to use the normalized pulse-wave volume (NPV) or the normalized pulse-wave volume converted to a logarithmic value (ln NPV) rather than the photoelectric volume pulse wave as the pulse-wave data to detect vascular baroreflex-related sympathetic activity. The reasons will be described below.

First, as shown in FIG. 2A, when a photoelectric volume pulse wave of the biological artery is measured, according to Lambert-Beer's law, light from a light source is absorbed when passing through a solution with a single layer in proportional to a concentration of the solution and a thickness of the liquid layer through which the light passes. Therefore, as shown in FIG. 2B, the AC component (PGac) of the photoelectric volume pulse wave can be calculated by amplifying the pulsating component of the artery in the DC component (PGdc).

However, as shown in FIGS. 2A and 2B, the actual living body includes a non-pulsating component when the artery is not pulsating and an individual difference component such as a fixed component corresponding to a tissue of the living body as a liquid layer when light passes through the living body. For this reason, the AC component (PGac) of the photoelectric volume pulse wave can only be used as a relative value which cannot be compared among different individuals. Therefore, a normalized pulse-wave volume (NPV) is known as an absolute value comparable even among different individuals, which is a normalized blood volume involved in pulsation obtained by dividing the AC component (PGac) of the photoelectric volume pulse wave by the DC component (PGdc) thereof (Non-Patent Literature 1).

Since the normalized pulse-wave volume (NPV) is calculated by division between the same units (mV) as described above, it can be said to be an absolute amount which is a dimensionless amount of blood volume involved in pulsation. Therefore, it is possible to compare not only measurement results acquired on different dates and times for a certain individual but also measurement results acquired for different individuals. There is also a merit that errors caused by a tissue component of the living body are excluded. Therefore, use of the normalized pulse-wave volume (NPV) or normalized pulse-wave volume converted to a logarithmic value (ln NPV) as pulse-wave data to detect vascular baroreflex-related sympathetic activity is recommended in the present invention.

Note that when the normalized pulse-wave volume (NPV) is evaluated by $\Delta I/I$, the transmitted light amount (AI) corresponding to the pulsation change is determined by the amplitude of the AC component of the pulse wave. Furthermore, the transmitted light amount (I) of the living body (tissue+blood) is determined by a mean value of the DC component of a pulse wave at the same time. Therefore, the pulse-wave data converting unit 42 calculates a normalized pulse-wave volume (NPV) obtained by dividing the amplitude of the AC component of the pulse wave by a mean value of the DC component of the pulse wave at the same time for each pulse based on pulse-wave data (photoelectric volume pulse wave) acquired by the pulse-wave data acquiring unit 41 and stores the normalized pulse-wave volume (NPV) in the pulse-wave data storing unit 32 in time series.

The pulse-wave data converting unit 42 may further convert the normalized pulse-wave volume (NPV) calculated for each pulse to a logarithmic value and store the normalized pulse-wave volume converted to the logarithmic value (ln NPV) in the pulse-wave data storing unit 32 in time series. On the other hand, as described above, when the pulse-wave data acquiring unit 41 acquires the normalized pulse-wave volume (NPV) converted in advance on the pulse-wave detecting means 2 side or the normalized pulse-wave volume converted to a logarithmic value (ln NPV) as pulse-wave data, the pulse-wave data converting unit 42 is unnecessary.

The beat-interval acquiring unit 43 acquires a beat interval corresponding to the pulse-wave data. In the present invention, as shown in FIG. 3, the "beat interval" is a concept including all time intervals corresponding to one beat of pulsation such as beat interval (PI) in pulse-wave data, interval of a portion where the AC component of the pulse-wave data rises (RI: hereinafter referred to as "rising interval") and heartbeat interval (RR interval) in cardiogram data.

In the present invention, the "beat interval corresponding to pulse-wave data" is a concept including not only a beat interval in the same time zone as the time zone in which pulse-wave data is acquired but also a beat interval delaying by one beat from the time zone in which pulse-wave data is acquired. More specifically, when the beat interval is a heartbeat interval, as shown in FIG. 3, not only heartbeat intervals a, b and c but also heartbeat intervals b, c and d correspond to the "beat interval corresponding to the pulse-wave data" with respect to pulse waves A, B and C.

Therefore, in the present embodiment, the beat-interval acquiring unit 43 acquires a beat interval or a rising interval corresponding to the pulse-wave data with reference to the pulse-wave data stored in the pulse-wave data storing unit 32 and stores the beat interval or the rising interval in the beat-interval storing unit 33 in time series. Note that the present embodiment provides cardiogram data separately for the electrocardiogram data storing unit 34 for older people or the like for whom it is hard to distinguish a beat interval or rising interval. In this case, the beat-interval acquiring unit 43 acquires heartbeat intervals corresponding to pulse-wave data with reference to the cardiogram data and stores the heartbeat intervals in the beat-interval storing unit 33 in time series.

The VBRSA-series detecting unit 44 detects a vascular baroreflex-related sympathetic activity series (VBRSA-series) indicating vascular baroreflex-related sympathetic activity from pulse-wave data. The vascular baroreflex-related sympathetic activity series is affected not by the neurogenic baroreflex function of the heart but by the sympathetic nervous system of the blood vessel associated with the neurogenic baroreflex function of the blood vessel. Hereinafter, the method for detecting a VBRSA-series from the normalized pulse-wave volume (NPV) of the pulse-wave data will be described more specifically, but other pulse-wave data can also be considered in the like manner.

As described above, the normalized pulse-wave volume (NPV) has a merit that measurement results can be compared among different individuals and errors caused by the tissue component of the living body are excluded. However, the normalized pulse-wave volume (NPV) is affected by both a single cardiac output (pulsating change of blood volume) using a baroreflex function (sympathetic nerve) of the heart as a mechanism and vascular resistance (vasoconstriction degree) using the baroreflex function (sympathetic nerve) of the blood vessel as a mechanism.

For this reason, as shown in FIGS. 4A and 4B, for a data series in which a systolic blood pressure (SBP) and a normalized pulse-wave volume (NPV) repeat a positive correlation loop, the baroreflex function of the heart functions dominantly and the data series is considered to be a cardiac baroreflex dominant series depending on a single cardiac output. On the other hand, for a data series considerably deviating from the above positive correlation loop, the normalized pulse-wave volume (NPV) indicates a completely different value, and so the baroreflex function of the blood vessel functions dominantly and the data series is considered to be a vascular baroreflex dominant series depending on vascular resistance. Note that in FIG. 4B, data of the cardiac baroreflex dominant series is represented by white circles (○) and data of the vascular baroreflex dominant series is represented by black circles (●).

That is, as shown by a single-dot dashed line in FIG. 4B, even when the systolic blood pressure (SBP) has the same value, the value of the normalized pulse-wave volume (NPV) considerably differs depending on which mechanism of the baroreflex function of the heart or the baroreflex function of the blood vessel is functioning dominantly. For this reason, even when the normalized pulse-wave volume (NPV) is used as is, it lacks independency as the index.

As shown in FIGS. 5A and 5B, there is also a data series (black circles in FIG. 5) that deviates from the data series (white circles in FIG. 5) that repeats the positive correlation loop in a scattered graph of the systolic blood pressure (SBP) and the beat interval (heartbeat interval RRI) and a scattered graph of the normalized pulse-wave volume (NPV) and the beat interval (heartbeat interval RRI). Therefore, it is only necessary to be able to detect the deviating data series in order to detect vascular baroreflex-related sympathetic activity associated with the baroreflex function of the blood vessel from the normalized pulse-wave volume (NPV) independently.

Focusing on a time zone A in measured data in FIG. 6, as shown in FIG. 7A, a positive correlation holds in data series of three or more beats made up of the normalized pulse-wave volume (NPV) and beat interval (beat interval IBI), and so this can be said to be neurogenic baroreflex-series of the heart (Patent Literature 1). Note that the neurogenic baroreflex sensitivity of the heart (cardiac nBRS: cardiac neural baroreflex sensitivity) is calculated by an inclination (regression coefficient) of a regression line indicating a correlation between the normalized pulse-wave volume (NPV) and the beat interval (IBI), and it is 19.2 (ms/unitless) in the example shown in FIG. 7A. On the other hand, in a time zone B in the measured data in FIG. 6, the normalized pulse-wave volume (NPV) increases at the third beat whereas the beat interval (IBI) decreases for three beats consecutively, as shown in FIG. 7B.

That is, the theoretical value of the normalized pulse-wave volume (NPV) at the third beat estimated from the neurogenic baroreflex-series of the heart is a smaller value than the value of the second beat as shown in FIG. 7B, whereas the measured value of the normalized pulse-wave volume (NPV) at the third beat is larger than the value of the second beat, and is deviated from the theoretical value. Such a series is considered affected not by parasympathetic autonomic nervous activity in the neurogenic baroreflex-series of the heart but by vascular sympathetic nervous activity, and so the series can be said to be a vascular baroreflex-related sympathetic activity series according to the present invention. Note that a VBRSA value which is an index indicating vascular baroreflex-related sympathetic activity (vascular BRSA) and which will be described later is calculated by |theoretical value−measured value| according to, for example, equation (1) below and is 4.84 (unitless) in the example shown in FIG. 7B.

As described above, the VBRSA-series detecting unit 44 of the present embodiment refers to the pulse-wave data in the pulse-wave data storing unit 32 and the beat interval in the beat-interval storing unit 33 and searches for series in which the beat interval increases or decreases by n (n is a natural number of 3 or more) beats consecutively. From among the series, the VBRSA-series detecting unit 44 detects series in which the correlation coefficient between the beat interval and pulse-wave data is greater than any positive threshold up to the (n−1)-th beat and the correlation coefficient is equal to or less than the threshold at the n-th beat as vascular baroreflex-related sympathetic activity series (VBRSA-series) indicating vascular baroreflex-related sympathetic activity and stores the series in the VBRSA-series storing unit 35 in time series.

Note that in the present invention, n, the number of continuous beats at which series are detected as the vascular baroreflex-related sympathetic activity series is assumed to be a natural number of 3 or more because the series are not affected by the sympathetic nervous system up to the (n−1)-th beat and it is intended to secure reliability that the series are affected by vascular sympathetic nervous activity involved in the baroreflex function from the n-th beat onward. Furthermore, 0.85 is adopted as the positive threshold in the present embodiment, but the present embodiment is not limited to this value.

The theoretical value calculating unit 45 calculates a theoretical value of the pulse-wave data at the n-th beat estimated from the neurogenic baroreflex-series of the heart. The theoretical value calculating unit 45 of the present embodiment refers to data of the vascular baroreflex-related sympathetic activity series stored in the VBRSA-series storing unit 35. The theoretical value calculating unit 45 then calculates a theoretical value of the pulse-wave data at the n-th beat estimated by a regression analysis between a beat interval corresponding to n beats and pulse-wave data corresponding to (n−1) beats in the data series.

More specifically, the theoretical value calculating unit 45 performs a regression analysis (linear regression or the like) between a beat interval corresponding to (n−1) beats and pulse-wave data, and calculates a regression line in the vascular baroreflex-related sympathetic activity series first. The theoretical value calculating unit 45 calculates the value obtained by assigning the beat interval at the n-th beat to the regression line as the theoretical value of pulse-wave data at the n-th beat.

The VBRSA value calculating unit 46 calculates a VBRSA value, which is an index indicating vascular baroreflex-related sympathetic activity. The VBRSA value calculating unit 46 in the present embodiment calculates a VBRSA value which is an index indicating the vascular baroreflex-related sympathetic activity based on the theoretical value of the pulse-wave data at the n-th beat calculated by the theoretical value calculating unit 45 and the measured value of the pulse-wave data at the n-th beat stored in the VBRSA-series storing unit 35.

More specifically, the VBRSA value calculating unit 46 calculates the VBRSA value using any one of equations (1) to (3) below:

$$\text{VBRSA value} = |PVt - PVm| \quad \text{equation (1)}$$

$$\text{VBRSA value} = |\ln(PVt) - \ln(PVm)| \quad \text{equation (2)}$$

$$\text{VBRSA value} = |PVt/PVm| \quad \text{equation (3)}$$

where, the respective symbols represent the following values:

PVt: theoretical value of pulse-wave data
PVm: measured value of pulse-wave data.

Note that when a photoelectric volume pulse wave is used as pulse-wave data, the "measured value" in the present invention refers to a value of actually measured photoelectric volume pulse wave. When a normalized pulse-wave volume (NPV) or a normalized pulse-wave volume converted to a logarithmic value (ln NPV) is used as the pulse-wave data, the "measured value" refers to a value converted from the photoelectric volume pulse wave. The method for calculating the VBRSA value is not limited to equations (1) to (3) above, but any equation may be adopted if it can calculate an index suitable for evaluating vascular baroreflex-related sympathetic activity using a theoretical value and measured value relating to pulse-wave data at the n-th beat.

The VBRSA value calculating unit 46 of the present embodiment may individually calculate the VBRSA value by dividing it into data series of the same type. More specifically, such data series refer to an ascending series among VBRSA series in which the beat interval increases by n beats consecutively and a descending series among VBRSA series in which the beat interval decreases by n beats consecutively.

The VBRSA value calculated for the ascending series serves as an index functioning to prevent excessive increase of a blood pressure. Furthermore, the VBRSA value calculated for the descending series serves as an index functioning to prevent excessive decrease of a blood pressure. Since the respective VBRSA values may differ depending on diseases (e.g., diabetes), separately calculating the VBRSA values is considered to improve evaluation accuracy.

On the other hand, the VBRSA value calculating unit 46 may calculate a total value of the ascending series and the descending series as a VBRSA value. More specifically, a VBRSA value may be obtained by totaling or averaging a mean value of VBRSA values calculated for the ascending series within a predetermined time (one minute or the like) and a mean value of VBRSA values calculated for the descending series within a predetermined time (one minute or the like). In this way, the number of cases increases where the VBRSA-series can be calculated even if the number of detected VBRSA-series is small, and the VBRSA value can also be used as an easy-to-understand index relating to vascular baroreflex-related sympathetic activity.

Next, operation of the vascular baroreflex-related sympathetic activity detection device 1 executed by the vascular baroreflex-related sympathetic activity detection program 1a of the present embodiment and the vascular baroreflex-related sympathetic activity detection method will be described with reference to FIG. 8.

When measuring vascular baroreflex-related sympathetic activity using the vascular baroreflex-related sympathetic activity detection device 1 or the vascular baroreflex-related sympathetic activity detection program 1a of the present embodiment, the pulse-wave data acquiring unit 41 acquires pulse-wave data of the biological artery from the pulse-wave detecting means 2 (step S1: pulse-wave data acquiring step), first. Since the pulse-wave data is simply and non-invasively measured according to an aspect of the pulse-wave detecting means 2, burden on the person to be measured is alleviated. Furthermore, when the pulse-wave detecting means 2 is a wearable one, daily or continuous measurement also becomes easier.

Next, the pulse-wave data converting unit 42 converts the photoelectric volume pulse wave as the pulse-wave data acquired in step S1 to a normalized pulse-wave volume (NPV) or the like (step S2: pulse-wave data conversion step). This eliminates individual difference components such as the aforementioned non-pulsating components or fixed components in the converted pulse-wave data. Therefore, not only measurement results acquired for a certain individual at different dates and times but also measurement results acquired for different individuals become comparable. Errors caused by tissue components of a living body are excluded.

Note that in the present embodiment, since the pulse-wave data acquiring unit 41 acquires the photoelectric volume pulse wave as the pulse-wave data, the vascular baroreflex-related sympathetic activity detection device 1 side converts the pulse-wave data (step S2). However, as described above, when the normalized pulse-wave volume (NPV) or the normalized pulse-wave volume converted to a logarithmic value (ln NPV) is acquired from the pulse-wave detecting means 2 as pulse-wave data, step S2 is skipped and the process jumps from step S1 to step S3.

Next, when the beat-interval acquiring unit 43 acquires a beat interval corresponding to the pulse-wave data (step S3: beat interval acquiring step), the VBRSA-series detecting unit 44 detects, from among a series in which the beat interval increases or decreases by n (n is a natural number of 3 or more) beats consecutively, series in which a correlation coefficient between the beat interval and the pulse-wave data is greater than any positive threshold up to the (n−1)-th beat and the correlation coefficient falls to or below the threshold at the n-th beat, as the vascular baroreflex-related sympathetic activity series (VBRSA-series) (step S4: VBRSA-series detection step). As a result, of the autonomic nervous system associated with the baroreflex function, the data series indicating the vascular baroreflex-related sympathetic activity affected by the sympathetic nervous system of the blood vessel, not the parasympathetic nervous system of the heart is identified separately and independently.

Next, the theoretical value calculating unit 45 calculates a theoretical value of pulse-wave data at the n-th beat by a regression analysis between the beat interval corresponding to n beats and pulse-wave data corresponding to (n−1) beats in the vascular baroreflex-related sympathetic activity series (step S5: theoretical value calculation step). In this way, even at the n-th beat, the pulse-wave data which should have been measured when the neurogenic baroreflex function of the heart is working is calculated as an estimated value.

Finally, the VBRSA value calculating unit 46 calculates a VBRSA value based on the theoretical value calculated in step S5 and the measured value of the pulse-wave data at the n-th beat (step S6: VBRSA value calculation step). This makes it possible to simply and objectively evaluate vascular baroreflex-related sympathetic activity using the VBRSA value. A VBRSA value suitable for evaluating vascular baroreflex-related sympathetic activity is calculated using any one of equations (1) to (3) above.

The VBRSA value calculating unit 46 in the present embodiment may individually calculate VBRSA values for the ascending series and the descending series respectively. When the VBRSA values in both series show a tendency which varies depending on diseases, the evaluation accuracy improves. Furthermore, the VBRSA value calculating unit 46 may calculate a total value of the ascending series and the descending series as a VBRSA value. This increases the number of cases increases where the VBRSA-series can be calculated even when the number of detected VBRSA-series is small. Furthermore, the index indicating vascular baroreflex-related sympathetic activity is expressed in an easily understandable way.

According to the embodiment of the present invention described so far, the following effects are provided.
1. Baroreflex vascular sympathetic nervous activity which is vascular sympathetic nervous activity involved in a baroreflex function can be simply and non-invasively detected individually.
2. Baroreflex vascular sympathetic nervous activity can be indexed as a VBRSA value and vascular baroreflex-related sympathetic activity can be simply and objectively evaluated.
3. A VBRSA value which is suitable for evaluating vascular baroreflex-related sympathetic activity can be calculated using any one of equations (1) to (3) above.
4. It is possible to grasp a tendency which varies depending on diseases and improve the evaluation accuracy by individually calculating VBRSA values for the ascending series and the descending series respectively.
5. It is possible to calculate the VBRSA values even when the number of detected VBRSA series is a small by calculating a total value of the ascending series and the descending series as a VBRSA value and thereby express an index indicating vascular baroreflex-related sympathetic activity in an easily understandable way.
6. It is possible to exclude errors caused by a tissue component of a living body using a normalized pulse-wave volume (NPV) which is a non-dimensional absolute amount and a normalized pulse-wave volume converted to a logarithmic value (ln NPV) and thereby compare not only measurement results of the same individual but also measurement results among different individuals and widely and generally grasp the trend of vascular baroreflex-related sympathetic activity.
7. It is possible to continuously monitor an autonomic nerve function for adjusting a blood pressure even in daily life by making the pulse-wave detecting means 2 wearable.
8. It is also possible to use the VBRSA value as an index indicating the baroreflex function of the blood vessel (neurogenic baroreflex sensitivity of the blood vessel) by converting a relationship with other measured values such as a blood pressure to a function.
9. It is possible to separately measure neurogenic baroreflex sensitivity of the heart from the pulse-wave data and thereby widely investigate and research a blood pressure adjusting function and a blood pressure state for each person to be measured by evaluating the relationship with vascular baroreflex-related sympathetic activity.
10. Using cardiogram data, it is possible to acquire an accurate beat interval even from a person to be measured from whom it is difficult to read a beat interval in pulse wave.
11. There is a possibility to provide the number of vascular baroreflex-related sympathetic activity series (VBRSA-series) and a detection frequency per unit time as medically useful information.

Next, specific examples of the vascular baroreflex-related sympathetic activity detection device 1, the vascular baroreflex-related sympathetic activity detection program 1a and the vascular baroreflex-related sympathetic activity detection method according to the present invention will be described.

EXAMPLE 1

In present Example 1, an experiment was conducted for confirming relevance with the vascular resistance controlled by the vascular baroreflex-related sympathetic activity and sympathetic nervous activity of the blood vessel (neurogenic baroreflex function of the blood vessel) according to the present invention based on hemodynamics that vary due to mental stress.

More specifically, a blood pressure meter (model name: MUB101, manufacturer: Medisens Co., Ltd.) for measuring blood pressure (BP) was attached to a finger of one examinee (aged 23, male) in supine position. Furthermore, a pulse-wave detecting means 2 (model name: EBRS-01J, manufacturer: Niche Product Co., Ltd.) for measuring photoelectric volume pulse wave was worn on an ear of the examinee. Furthermore, an ultrasound probe (model name: UNEXEF38G, manufacturer: UNEX Corporation) was fixed to the neck of an examinee to measure a cardiac output in the carotid using a Doppler method.

Respective pieces of the aforementioned data were simultaneously measured in time series for 9 minutes. Of the 9 minutes, the examinee was asked to rest for first 3 minutes (Rest). In the next 3 minutes, the examinee was asked to perform difficult mental arithmetic for the purpose of loading mental stress (Stress). During the last 3 minutes, the examinee was asked to rest again and recover (Recovery).

The measured cardiac output was processed by a blood vessel endothelium function test apparatus (model name: UNEXEF38G, manufacturer: UNEX Corporation) to calculate a mean blood pressure (MBP) and a cardiac output, and calculate vascular resistance of the carotid (carotid arterial resistance) based on hemodynamic (mean blood pressure=cardiac output×vascular resistance). The measured photoelectric volume pulse wave was processed by the vascular baroreflex-related sympathetic activity detection device 1 according to the present invention, and a normalized pulse-wave volume (NPV), a pulsation interval (IBI) and a VBRSA value (vascular BRSA) were calculated. The results are shown in FIG. 9.

FIG. 9 is a diagram illustrating measurement results obtained about the examinee in time series. Of the measurement results, FIG. 10 shows a scattered graph plotting a mean value every 10 seconds for the VBRSA value (vascular BRSA) and vascular resistance of the carotid (carotid arterial resistance). Note that in FIG. 10, white circles are data representing rest time (Rest), black circles are data representing stress load time (Stress), white triangle are data representing recovery time (Recovery).

As shown in FIG. 10, at the time of stress load, the pulsation interval is reduced by approximately half compared to the rest time, and the pulse rate is increased to approximately twice. In addition, at the time of stress load, it is observed that the vascular resistance increases compared to the rest time, and the blood vessel is tensioned and hardened. At this time, the trend of the VBRSA value (vascular BRSA) shows a high value at rest when the vascular resistance is low and works so that the blood vessel does not relax further. On the other hand, at the time of stress load when the vascular resistance is high, it shows a low value and does not work very much. Such a result agrees with the sympathetic nervous activity of the blood vessel measured by conventional microneurography.

According to present Example 1 above, it has been confirmed that there is a theoretically proven relevance between the vascular baroreflex-related sympathetic activity according to the present invention and vascular resistance controlled by the sympathetic nervous activity of the blood vessel (neurogenic baroreflex function of the blood vessel). Furthermore, it has been shown that the VBRSA value according to the present invention can be used as an index indicating vascular baroreflex-related sympathetic activity.

EXAMPLE 2

In present Example 2, an experiment was conducted to confirm whether or not vascular baroreflex-related sympathetic activity according to the present invention has relevancy with vascular resistance for a person whose reaction mechanism that causes blood pressure to ascend against mental stress acts dominantly on either the baroreflex function of the heart or the baroreflex function of the blood vessel.

More specifically, for each of nine male examinees and two female examinees aged 20 to 25, the same measurement and analysis as those in Example 1 were applied and the aforementioned various kinds of data were calculated. On which baroreflex function, the reaction mechanism that causes blood pressure to ascend against the aforementioned mental stress acts dominantly varies from one individual to another. Therefore, in present Example 2, all examinees were classified into either a cardiac-dominated reaction group for whom blood pressure is caused to ascend mainly by cardiac output (therefore, vascular resistance decreases) or a vascular-dominated reaction group for whom blood pressure is caused to ascend mainly by vascular resistance.

Average values and standard deviations of mean blood pressure (MBP), vascular resistance of the carotid (carotid arterial resistance) and VBRSA value (vascular BRSA) at the time of rest (Rest), stress load (Stress) and recovery (Recovery) were respectively made into a graph for the cardiac-dominated reaction group and the vascular-dominated reaction group. FIGS. 11A to 11C show the results. Note that black circles represent data of the vascular-dominated reaction group and white circles represent data of the cardiac-dominated reaction group.

FIG. 12 shows a correlation diagram between the VBRSA value (vascular BRSA) and vascular resistance of the carotid (carotid arterial resistance) created using measured data of all the examinees. In present example 2, Pearson correlation coefficient between the two was −0.61 and was significant at 1% level. As shown in FIG. 11 and FIG. 12, relevancy of the VBRSA value (vascular BRSA) according to the present invention with vascular resistance of the carotid (carotid arterial resistance) was confirmed for both the cardiac-dominated reaction group and the vascular-dominated reaction group.

According to present Example 2 described so far, it has been confirmed that the vascular baroreflex-related sympathetic activity according to the present invention has relevancy with vascular resistance irrespective of which type of people the reaction mechanism for causing blood pressure to ascend against mental stress acts dominantly for the baroreflex function of the heart or the baroreflex function of the blood vessel. Therefore, it has been confirmed that the VBRSA value according to the present invention can be used as an index capable of evaluating vascular baroreflex-related sympathetic activity irrespective of individual differences associated with the reaction mechanism.

EXAMPLE 3

In present Example 3, an experiment was conducted to confirm whether or not the VBRSA value has reliability as an index for evaluating vascular baroreflex-related sympathetic activity based on relevancy between the VBRSA value according to the present invention and diastolic blood pressure caused by relaxation of blood vessel.

More specifically, a portable automatic sphygmomanometer (model name: TM-2431, manufacturer: A&D Company, Limited) was worn on the upper arm of an examinee (aged 22, male) to measure a blood pressure fluctuation. Furthermore, pulse-wave detecting means 2 (model name: EBRS-01J, manufacturer: Niche Product Co., Ltd.) was attached to an ear of the examinee to measure a photoelectric volume pulse wave. The aforementioned various pieces of data were simultaneously measured in time series over such a long period of time of one or more hours before sleep, during sleep and one or more hours after sleep.

The measured blood pressure data was then processed using blood pressure analysis software (model name: TM-2430-15, manufacturer: A&D Company, Limited) and the diastolic blood pressure (DBP) was calculated. Furthermore, the measured photoelectric volume pulse wave was processed by the vascular baroreflex-related sympathetic activity detection device 1 according to the present invention, and pulsation interval (IBI), normalized pulse-wave volume (NPV) and VBRSA value (vascular BRSA) were calculated. FIG. 13 shows the results.

Note that the examinee recorded contents and time about his own action event (Event) during the measurement period. What is recorded as Event1 in FIG. 13 corresponds to a time at which the examinee went to the toilet. Event2 corresponds to bedtime and Event3 corresponds to a wake-up time. In present Example 3, the period from the bedtime to the wake-up time is considered as a sleeping period (Sleep) and other periods are considered as an awake period (Awake).

It is generally estimated that a pulse rate of a healthy young person is lowered (pulsation interval increases) and blood pressure drops due to relaxation of the blood vessel during sleep. In this respect, in present Example 3, the pulsation interval (IBI) increases during sleep (Sleep) as shown in FIG. 13 and the diastolic blood pressure (DBP) drops, confirming that the estimated result was obtained.

FIG. 14 is a graph illustrating a mean value (vascular BRSA) of the VBRSA value according to the present invention and the diastolic blood pressure (DBP) during a blood pressure measurement time of the measured data shown in FIG. 13. As shown in FIG. 14, a high correlation is confirmed between the VBRSA value and the diastolic blood pressure, and the correlation coefficient was −0.94. Note that the inclination of a regression line indicating a correlation between the VBRSA value and the diastolic blood pressure can also be used as an index for indicating the baroreflex function of the blood vessel (neurogenic baroreflex sensitivity of the blood vessel).

According to present Example 3 described so far, it has been proved that the VBRSA value according to the present invention has high reliability as an index for evaluating vascular baroreflex-related sympathetic activity corresponding to a diastolic blood pressure due to relaxation of the blood vessel even in daily life.

Note that the vascular baroreflex-related sympathetic activity detection device 1, the vascular baroreflex-related sympathetic activity detection program 1a and the vascular baroreflex-related sympathetic activity detection method according to the present invention are not limited to the aforementioned embodiment and examples but can be changed as appropriate.

For example, a display table showing evaluations (e.g.: good, average, poor) in association with a numerical value range of the VBRSA value according to the present invention may be stored in the storing means 3, an evaluation relating to vascular baroreflex-related sympathetic activity may be outputted from display means or printing means based on the VBRSA value calculated by the VBRSA value calculating unit 46 and may be presented to a person to be measured.

In the aforementioned present example, the normalized pulse-wave volume (NPV) is used as pulse-wave data to detect vascular baroreflex-related sympathetic activity, but the present invention is not necessarily limited to this. That is, when the normalized pulse-wave volume (NPV) is used only as a relative value which cannot be compared among individuals, the value of the photoelectric volume pulse wave may be used as is.

INDUSTRIAL APPLICABILITY

Blood pressure is an important risk factor for cardiovascular diseases which is on the increase in the advanced elderly society. By applying measurement of vascular baroreflex-related sympathetic activity with high reliability to daily life, it is possible to monitor and examine a mechanism for adjusting a blood pressure more specifically.

Therefore, the present invention contributes to disease prediction, screening, diagnosis and long-term follow-up examination at a pre-clinical stage of all lifestyle-related diseases including chronic cardiac failure and has an extremely wide ripple effect on medical sites.

Furthermore, when the vascular baroreflex-related sympathetic activity measuring device 1 according to the present invention is miniaturized to a portable terminal size of a smartphone or tablet terminal or the like, it may be widely available for household or individual applications as a health apparatus that can be easily handled from children to the elderly. Furthermore, use in combination with the wearable pulse-wave detecting means 2 may be considered to further facilitate monitoring in daily life.

REFERENCE SIGNS LIST 1 vascular baroreflex-related sympathetic activity detection device
1a vascular baroreflex-related sympathetic activity detection program
2 pulse-wave detecting means
3 storing means
4 arithmetic processing means
21 photo-sensor
21a light emitting unit
21b light receiving unit
22 pulse wave amplifier
31 program storing unit
32 pulse-wave data storing unit
33 beat-interval storing unit
34 electrocardiogram data storing unit
35 VBRSA-series storing unit
36 VBRSA value storing unit
41 pulse-wave data acquiring unit
42 pulse-wave data converting unit
43 beat-interval acquiring unit
44 VBRSA-series detecting unit
45 theoretical value calculating unit
46 VBRSA value calculating unit

The invention claimed is:

1. A vascular baroreflex-related sympathetic activity (VBRSA) detection device that detects vascular sympathetic nervous activity involved in a baroreflex function, the device comprising:
a storage device that stores pulse-wave data of a biological artery received from a pulse-wave detecting device and data of a VBRSA-series;
a processor configured to function as:
a VBRSA-series detecting unit that
detects at least one beat interval series in which a beat interval increases or decreases for n (n is a natural number of 3 or more) beats consecutively counting from a reference beat, and
identifies the VBRSA-series in the detected at least one beat interval series, the VBRSA-series being a beat interval series in which a correlation coefficient between the beat interval and the pulse-wave data corresponding to the beat interval is greater than a positive threshold up to an (n-1)-th beat and the correlation coefficient falls to or below the positive threshold at an n-th beat as a VBRSA series indicating the VBRSA;
a beat-interval acquiring unit that determines beat intervals from the pulse-wave data stored in the storage device;

a theoretical value calculating unit that calculates, in the VBRSA series, a theoretical value of the pulse-wave data at the n-th beat through a regression analysis between (1) the beat intervals for the n beats counting from the reference beat and (2) the pulse-wave data for the (n-1) beats counting from the reference beat and a VBRSA value calculating unit that calculates a VBRSA value for the VBRSA-series based on a measured value of the pulse-wave data at the n-th beat of the beat interval and the theoretical value, wherein the VBRSA value is an index for evaluating the vascular baroreflex-related sympathetic activity.

2. The VBRSA detection device according to claim 1, wherein the VBRSA value calculating unit calculates the VBRSA value using any one of equations (1) to (3) below:

$$\text{VBRSA value} = |PVt - PVm| \quad \text{equation (1)}$$

$$\text{VBRSA value} = |\ln(PVt) - \ln(PVm)| \quad \text{equation (2)}$$

$$\text{VBRSA value} = |PVt/PVm| \quad \text{equation (3)}$$

where, the respective symbols represent the following:
PVt: theoretical value of pulse-wave data
PVm: measured value of pulse-wave data.

3. The VBRSA detection device according to claim 1, wherein the VBRSA value calculating unit individually calculates VBRSA values for an ascending series in which the beat interval increases for the n beats consecutively in the VBRSA-series and VBRSA values for a descending series in which the beat interval decreases for the n beats consecutively in the VBRSA-series.

4. The VBRSA detection device according to claim 3, wherein the VBRSA value calculating unit calculates a value totaling or averaging a mean value of the VBRSA value calculated for the ascending series and a mean value of the VBRSA value calculated for the descending series as the VBRSA value.

5. The VBRSA detection device according to claim 1, wherein the pulse-wave data is any one of a photoelectric volume pulse wave, a normalized pulse-wave volume in which the photoelectric volume pulse wave is normalized, or a logarithmized pulse-wave volume in which the normalized pulse-wave volume is converted to a logarithmic value.

6. A non-transitory computer-readable recording medium storing a vascular baroreflex-related sympathetic activity (VBRSA) detection program for detecting vascular sympathetic nervous activity involved in a baroreflex function, the program causing a computer having a storage device to function as:

a VBRSA-series detecting unit that
detects at least one beat interval series in which a beat interval increases or decreases for n (n is a natural number of 3 or more) beats consecutively counting from a reference beat, and
identifies a VBRSA-series in the detected at least one beat interval series, the VBRSA-series being a beat interval series in which a correlation coefficient between the beat interval and pulse-wave data of a biological artery received from a pulse-wave detecting device that corresponds to the beat interval is greater than a positive threshold up to an (n-1)-th beat and falls to or below the positive threshold at an n-th beat;

a beat-interval acquiring unit that determines beat intervals from the pulse-wave data stored in the storage device;

a theoretical value calculating unit that calculates, in the VBRSA series, a theoretical value of the pulse-wave data at the n-th beat through a regression analysis between (1) the beat intervals for the n beats counting from the reference beat and (2) the pulse-wave data for the (n-(1) beats counting from the reference beat; and a VBRSA value calculating unit that calculates a VBRSA value for the VBRSA-series based on a measured value of the pulse-wave data at the n-th beat of the beat interval and the theoretical value, wherein the VBRSA value is an index for evaluating the vascular baroreflex-related sympathetic activity.

7. The non-transitory computer-readable recording medium storing a VBRSA detection program according to claim 6, wherein the VBRSA value calculating unit calculates the VBRSA value using any one of equations (1) to (3) below:

$$\text{VBRSA value} = |PVt - PVm| \quad \text{equation (1)}$$

$$\text{VBRSA value} = |\ln(PVt) - \ln(PVm)| \quad \text{equation (2)}$$

$$\text{VBRSA value} = |PVt/PVm| \quad \text{equation (3)}$$

where, the respective symbols represent the following:
PVt: theoretical value of pulse-wave data
PVm: measured value of pulse-wave data.

8. The non-transitory computer-readable recording medium storing the VBRSA program according to claim 7, wherein the VBRSA value calculating unit individually calculates VBRSA values for the ascending series in which the beat interval increases for the n beats consecutively in the VBRSA-series and VBRSA values for the descending series in which the beat interval decreases for the n beats consecutively in the VBRSA-series.

9. The non-transitory computer-readable recording medium storing the VBRSA detection program according to claim 8, wherein the VBRSA value calculating unit calculates a value totaling or averaging a mean value of the VBRSA value calculated for the ascending series and a mean value of the VBRSA value calculated for the descending series as the VBRSA value.

10. The non-transitory computer-readable recording medium storing the VBRSA detection program according to claim 7, wherein the pulse-wave data is any one of a photoelectric volume pulse wave, a normalized pulse-wave volume in which is the photoelectric volume pulse wave is normalized, or a logarithmized pulse-wave volume in which the normalized pulse-wave volume is converted to a logarithmic value.

11. A vascular baroreflex-related sympathetic activity (VBRSA) detection method for detecting vascular sympathetic nervous activity involved in a baroreflex function, the method comprising:

a VBRSA-series detection step of
detects at least one beat interval series in which a beat interval increases or decreases for n (n is a natural number of 3 or more) beats consecutively counting from a reference beat, and
identifies a VBRSA-series in the detected at least one beat interval series, the VBRSA-series being a beat interval series in which a correlation coefficient between the beat interval and pulse-wave data of a biological artery received from a pulse-wave detecting device that corresponds to the beat interval is greater than a positive threshold up to an (n-1)-th beat and falls to or below the positive threshold at an n-th beat;

a beat-interval acquiring step of determininges beat intervals from the pulse-wave data stored in a storage device;

a theoretical value calculation step of calculating, in the VBRSA series, a theoretical value of the pulse-wave data at the n-th beat through a regression analysis between (1) the beat intervals for the n beats counting from the reference beat and (2) the pulse-wave data for the (n-1) beats counting from the reference beat; and a VBRSA value calculation step of calculating a VBRSA value for the VBRSA-series based on a measured value of the pulse-wave data at the n-th beat of the beat interval and the theoretical value, wherein the VBRSA value is an index for evaluating the vascular baroreflex-related sympathetic activity.

12. The VBRSA detection method according to claim 11, wherein in the VBRSA value calculation step, the VBRSA value is calculated using any one of equations (1) to (3) below:

$$\text{VBRSA value} = |PVt - PVm| \quad \text{equation (1)}$$

$$\text{VBRSA value} = |\ln(PVt) - \ln(PVm)| \quad \text{equation (2)}$$

$$\text{VBRSA value} = |PVt/PVm| \quad \text{equation (3)}$$

where, the respective symbols represent the following:
PVt: theoretical value of pulse-wave data
PVm: measured value of pulse-wave data.

13. The VBRSA detection method according to claim 11, wherein in the VBRSA value calculation step, VBRSA values are individually calculated for the ascending series in which the beat interval increases for the n beats consecutively in the VBRSA-series and for the descending series in which the beat interval decreases for the n beats consecutively in the VBRSA-series.

14. The VBRSA detection method according to claim 13, wherein in the VBRSA value calculation step, a value totaling or averaging a mean value of the VBRSA value calculated for the ascending series and a mean value of the VBRSA value calculated for the descending series is calculated as the VBRSA value.

15. The VBRSA detection method according to claim 11, wherein the pulse-wave data is any one of a photoelectric volume pulse wave, a normalized pulse-wave volume in which is the photoelectric volume pulse wave is normalized, or a logatithmized pulse-wave volume in which the normalized pulse-wave volume is converted to a logarithmic value.

* * * * *